(12) United States Patent
Zhou et al.

(10) Patent No.: US 8,426,669 B2
(45) Date of Patent: Apr. 23, 2013

(54) ABSORBENT ARTICLE HAVING A SIGNAL COMPOSITE

(75) Inventors: Peiguang Zhou, Appleton, WI (US); Andrew Mark Long, Appleton, WI (US); Dave Allen Soerens, Neenah, WI (US); Kaiyuan Yang, Cumming, GA (US); Davis-Dang Hoang Nhan, Appleton, WI (US); Jun G. Zhang, Appleton, WI (US)

(73) Assignee: Kimberly-Clark Worldwide Inc., Neenah, WI (US)

( * ) Notice: Subject to any disclaimer, the term of this patent is extended or adjusted under 35 U.S.C. 154(b) by 542 days.

(21) Appl. No.: 12/646,763

(22) Filed: Dec. 23, 2009

(65) Prior Publication Data

US 2011/0152806 A1    Jun. 23, 2011

(51) Int. Cl.
    *A61F 13/15*    (2006.01)
(52) U.S. Cl.
    USPC .............................. 604/361; 604/364; 604/366
(58) Field of Classification Search ................... 604/361, 604/366, 367
    See application file for complete search history.

(56) References Cited

U.S. PATENT DOCUMENTS

| | | | |
|---|---|---|---|
| 5,649,914 A | 7/1997 | Glaug et al. | |
| 5,681,298 A | 10/1997 | Brunner et al. | |
| 5,702,377 A | 12/1997 | Collier, IV et al. | |
| 6,307,119 B1 | 10/2001 | Cammarota et al. | |
| 6,464,672 B1 | 10/2002 | Buckley | |
| 6,716,498 B2 | 4/2004 | Curro et al. | |
| 6,726,668 B2 | 4/2004 | Underhill et al. | |
| 6,929,819 B2 | 8/2005 | Underhill et al. | |
| 6,958,432 B2 | 10/2005 | Underhill et al. | |
| 7,002,055 B2 | 2/2006 | Long et al. | |
| 7,083,839 B2 | 8/2006 | Fish et al. | |
| 7,175,613 B2 | 2/2007 | Sugiyama et al. | |
| 7,250,548 B2 | 7/2007 | Weber et al. | |
| 7,297,835 B2 | 11/2007 | Olson | |
| 7,632,978 B2 | 12/2009 | Olson et al. | |
| 2002/0169427 A1 | 11/2002 | Roe et al. | |
| 2004/0122396 A1 | 6/2004 | Maldonado et al. | |

(Continued)

FOREIGN PATENT DOCUMENTS

KR    10-2008-0046414 A    5/2008

OTHER PUBLICATIONS

"Graphic Indicators for Training Pants," ISSN 0266-2078, discussion of K-C US Patent 6307119, *Medical Textiles*, Apr. 2002, 1 page.

*Primary Examiner* — Justine Yu
(74) *Attorney, Agent, or Firm* — Randall W. Fieldhack; Kenya Pierre

(57) ABSTRACT

An absorbent article comprises a signal composite comprising a carrier substrate layer, a first stimulation layer, a second stimulation layer, a first thermoplastic adhesive layer and a second thermoplastic adhesive layer. The carrier substrate layer is disposed as a bottom layer of the signal composite. The first stimulation layer comprises a first stimulation material and is disposed above and adjacent to the carrier substrate layer. The second stimulation layer comprises a second stimulation material and is disposed above and adjacent to the first stimulation layer to provide the body-facing surface of the signal composite. The first thermoplastic adhesive layer is liquid permeable or water-soluble and is disposed between and adjacent to the carrier substrate layer and the first stimulation layer. The second thermoplastic adhesive layer is liquid permeable or water-soluble and is disposed between the first stimulation layer and the second stimulation layer.

21 Claims, 9 Drawing Sheets

U.S. PATENT DOCUMENTS

| | | |
|---|---|---|
| 2004/0254550 A1 | 12/2004 | Huang et al. |
| 2005/0107759 A1 | 5/2005 | Waksmundzki et al. |
| 2005/0203473 A1 | 9/2005 | Pesce et al. |
| 2006/0142714 A1 | 6/2006 | Jackson et al. |
| 2006/0178071 A1* | 8/2006 | Schmidt et al. ............... 442/417 |
| 2007/0233026 A1 | 10/2007 | Roe et al. |
| 2007/0252713 A1 | 11/2007 | Rondoni et al. |
| 2007/0287971 A1 | 12/2007 | Roe et al. |
| 2008/0119812 A1 | 5/2008 | Hurwitz |
| 2008/0147153 A1 | 6/2008 | Quincy et al. |
| 2008/0269703 A1 | 10/2008 | Collins et al. |
| 2009/0054860 A1 | 2/2009 | Young et al. |
| 2011/0152816 A1 | 6/2011 | Zhou et al. |

* cited by examiner

ABSORBENT ARTICLE HAVING A SIGNAL COMPOSITE

BACKGROUND

The present invention relates to absorbent articles that include a stimulation material. More specifically, the invention relates to an absorbent article, such as training pants, that provides the wearer with a noticeable change in sensation upon fluid insult.

Absorbent articles, such as children's training pants for example, have been designed with temperature change particles to provide a temperature change sensation upon urination in an attempt to enhance a child's recognition of when urination occurs. As can be appreciated, such recognition can be an important step in the toilet training process. The temperature change sensation can often be the result of the stimulation material being positioned between the topsheet and the absorbent core of the article.

Unfortunately, in certain circumstances, the design of such articles may not be completely satisfactory. For example, the stimulation material included within the article can, in certain instances, be abrasive to the wearer. This abrasiveness can be particularly notable where the stimulation material is positioned close to the wearer's skin in use, which is generally a desirable configuration to maximize the temperature change sensation experienced by the wearer. In addition, the stimulation material can be unattached, thus resulting in shake-out or movement of the material. Moreover, the stimulation material may provide a rapid temperature change sensation, but it may not last as long as desired to assist with the toilet training process.

In addition, current articles may not provide a means for changing the stimulation effect and/or having more than one stimulation effect for a period of time after an aqueous insult has occurred. For example, it may be even more alerting to a user if an article provides a warming sensation upon insult, and then subsequently provides a cooling sensation thereafter, or alternatively provides a cooling sensation upon insult and then provides pressure or a tingling sensation to the user, or even providing both a cooling effect and a pressure change effect that can be sustained for 5 minutes or more.

In some circumstances, it may be desirable for a stimulation device in an article to do more than just alert the user of an insult. Indeed, it may be desirable for the stimulation device to additionally provide a benefit to the user. For example, in addition to alerting the user of an insult, the stimulation device could also provide pH buffering for the skin, vaginal health-care for a female, odor control, coating materials for skin health, or even medicines.

Thus, there is a need for a disposable absorbent article with a single stimulation device that can delay or prolong the effects of the stimulation material; that is capable of having more than one effect for a sustained period after at least one aqueous insult; that is capable of changing the stimulation effect after at least one insult; that secures the stimulation material to reduce or prevent movement of the material; and/or can provide additional benefits to the user.

SUMMARY

In response to the needs discussed above, an absorbent article comprises a signal composite, wherein the signal composite has a body-facing surface, a garment-facing surface, a longitudinal direction, a transverse direction and a z-direction. The signal composite comprises a carrier substrate layer, a first stimulation layer, a second stimulation layer, a first thermoplastic adhesive layer and a second thermoplastic adhesive layer. The carrier substrate layer is liquid permeable or water-soluble and is disposed as a bottom layer of the signal composite in the z-direction to provide the garment-facing surface of the signal composite. The first stimulation layer comprises a first stimulation material and is disposed above and adjacent to the carrier substrate layer. The second stimulation layer comprises a second stimulation material and is disposed above and adjacent to the first stimulation layer to provide the body-facing surface of the signal composite. The first thermoplastic adhesive layer is liquid permeable or water-soluble and is disposed between and adjacent to the carrier substrate layer and the first stimulation layer. The second thermoplastic adhesive layer is liquid permeable or water-soluble and is disposed between the first stimulation layer and the second stimulation layer. In addition, each stimulation layer comprises at least 50 wt % of stimulation material having a solubility of from 0.1 grams to 6 grams of material per gram of water. In further aspects, the carrier substrate layer has a basis weight of 10 gsm and 50 gsm. In still further aspects, the carrier substrate layer has a thickness in the z-direction of 0.1 mm and 1 mm, as measured by the Thickness Test. In yet further aspects, the carrier substrate layer is a nonwoven substrate. In still further aspects, the carrier substrate layer is a thermoplastic water-soluble polymer film. In yet further aspects, at least one of the first stimulation layer and the second stimulation layer comprises a stimulation material in the form of a cooling agent, wherein the cooling agent is selected from xylitol, sorbitol or urea. In still further aspects, the first stimulation layer comprises stimulation material in the form of a cooling agent and the second stimulation layer comprises stimulation material in the form of a warming agent. In yet further aspects, the first stimulation layer comprises stimulation material in the form of a cooling agent, and the second stimulation layer comprises stimulation material in the form of a cooling agent and a pressure change agent. In still further aspects, each of the first stimulation layer and the second stimulation layer has a basis weight of 25 gsm to 500 gsm. In yet further aspects, each of the first thermoplastic adhesive layer and the second thermoplastic adhesive layer is hydrophobic. In still further aspects, each of the first thermoplastic adhesive layer and the second thermoplastic adhesive layer has a basis weight of 2 gsm to 25 gsm. In yet further aspects, at least one of the first stimulation layer and the second stimulation layer further comprises a beneficial additive. In still further aspects, the signal composite has a thickness in the z-direction of 0.25 mm to 5 mm, as measured by the Thickness Test. In yet further aspects, each of the carrier substrate layer, first stimulation layer, second stimulation layer, first thermoplastic adhesive layer and second thermoplastic adhesive layer are coextensive in the longitudinal direction and in the transverse direction. In still further aspects, the signal composite comprises at least one additional stimulation layer and at least one additional thermoplastic adhesive layer, wherein the at least one additional stimulation layer is disposed above and adjacent the second stimulation layer, and wherein the at least one additional thermoplastic adhesive layer is liquid permeable or water-soluble and is disposed between and adjacent to the second stimulation layer and the at least one additional stimulation layer. In yet further aspects, the signal composite further comprises 1-13 additional stimulation layers, and 1-13 additional thermoplastic adhesive layers such that the additional thermoplastic adhesive layers and the additional stimulation layers are disposed in an alternating fashion. In still further aspects, the signal composite an additional liquid-pervious substrate layer and an additional thermoplastic adhesive layer, wherein the additional liquid-pervious substrate layer is disposed above and adjacent to the second stimulation layer, and wherein the additional thermoplastic adhesive layer is liquid permeable or water-soluble and is disposed between and adjacent to the second stimulation layer and the additional liquid-pervious stimulation layer.

In some aspects, an absorbent article comprises a signal composite, wherein the signal composite has a body-facing surface, a garment-facing surface, a longitudinal direction, a transverse direction and a z-direction. The signal composite comprises a carrier substrate layer, 2-15 stimulation layers, and 2-15 thermoplastic adhesive layers. The carrier substrate layer is liquid permeable or water-soluble and is disposed as a bottom layer of the signal composite in the z-direction to provide the garment-facing surface. The stimulation layers each comprise stimulation materials and are each disposed above and adjacent to the carrier substrate layer. In addition, one of the stimulation layers is disposed as a top layer of the signal composite in the z-direction to provide the body-facing surface. The each thermoplastic adhesive layer is liquid permeable or water-soluble. In addition, one of the thermoplastic adhesive layers is disposed between and adjacent to the carrier substrate layer and one of the stimulation layers, and each of the remaining thermoplastic adhesive layers is disposed between and adjacent to the remaining stimulation layers in an alternating fashion. Furthermore, at least 50 wt % of the stimulation materials in at least two stimulation layers have a solubility of from 0.1 grams to 6 grams of material per gram of water. The carrier substrate layer has a basis weight of 10 gsm and 50 gsm; each of the stimulation layers has a basis weight of 25 gsm to 500 gsm and each of the thermoplastic adhesive layers has a basis weight of 2 gsm to 25 gsm. In addition, the signal composite has a thickness in the z-direction of 0.25 mm and 5 mm, as measured by the Thickness Test. In further aspects, at least one of the stimulation layers further comprises a beneficial additive. In still further aspects, at least one of the stimulation layers comprises stimulation material in form of a cooling agent. In yet further aspects, the stimulation layers and the thermoplastic adhesive layers are coextensive in the longitudinal direction and in the transverse direction.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

FIGURES

The foregoing and other features, aspects and advantages of the present invention will become better understood with regard to the following description, appended claims and accompanying drawings.

FIG. 1 representatively illustrates a side view of a training pant with a mechanical fastening system of the pants shown fastened on one side of the training pant and unfastened on the other side of the training pant.

FIG. 2 representatively illustrates a plan view of the training pant of FIG. 1 in an unfastened, stretched and laid flat condition, showing the surface of the training pant that faces toward the wearer and having a signal composite of the present invention.

Figure 1:
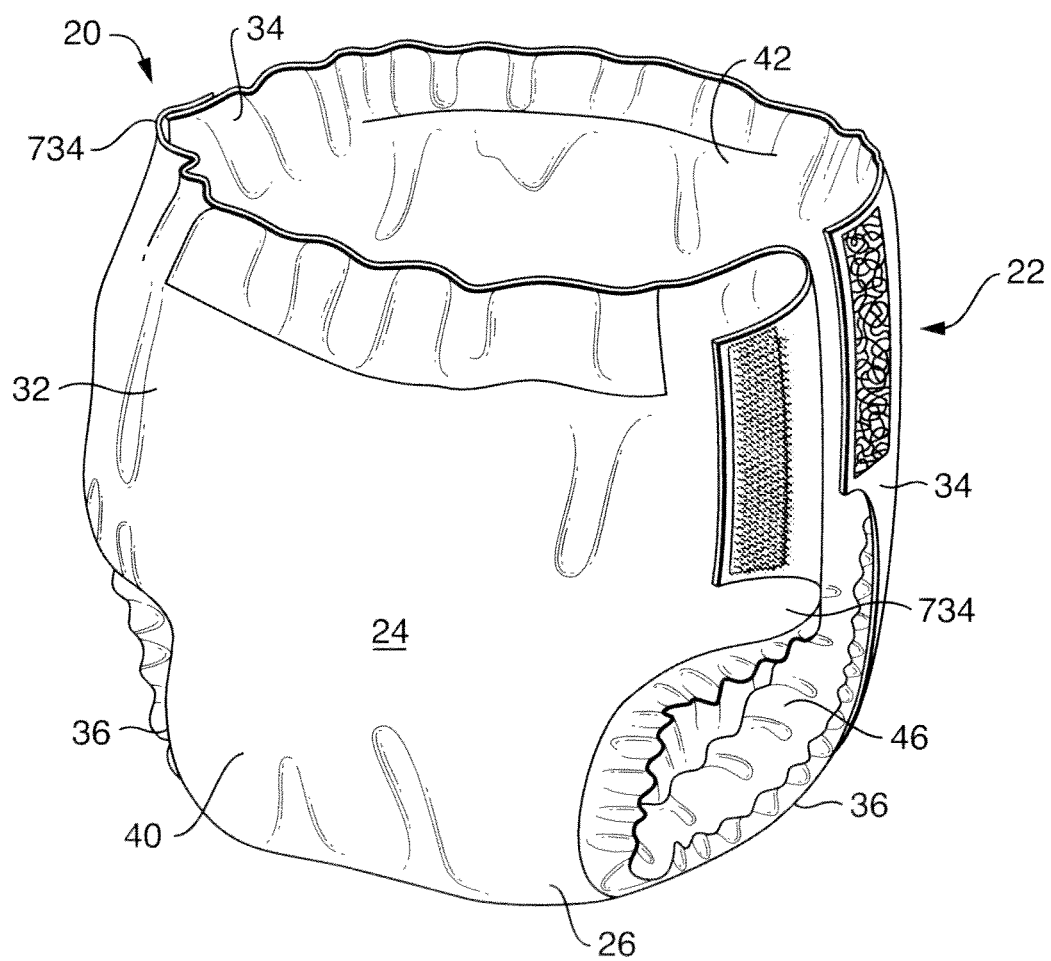

Repeated use of reference characters in the present specification and drawings is intended to represent the same or analogous features or elements of the present invention. The drawings are representational and are not necessarily drawn to scale. Certain proportions thereof may be exaggerated, while others may be minimized

TEST METHODS

Unless otherwise noted, all tests are performed at a temp of 23±2° C. and a relative humidity of 50±5%.

Particle Size Test

A stack of sieves are used to determine the particle size distribution of a given sample. Thus, for example, a particle that is retained on a sieve with 710 micron openings is considered to have a particle size greater than 710 microns. A particle that passes through a sieve having 710 micron openings and is retained on a sieve having 500 micron openings is considered to have a particle size between 500 and 710 microns. Further, a particle that passes through a sieve having 500 micron openings is considered to have a particle size less than 500 microns, and so on.

The sieves are placed in order of the size of the openings with the largest openings on the top of the stack and the smallest openings on the bottom of the stack. Thus, all of the stimulation material associated with a signal composite can be weighed and placed into the sieve with the largest openings. Alternatively, if it is desired to determine the particle size or particle size distribution of the stimulation material in only a particular portion of the signal composite, only the stimulation material associated with that portion can be weighed and placed into the sieve with the largest openings. U.S. Standard sieves can be used in the sieve stack, including 20 mesh (850 microns), 25 mesh (710 microns), 35 mesh (500 microns), 50 mesh (300 microns) and 170 mesh (90 microns).

The sieve stack is shaken for 10 minutes with a Ro-Tap mechanical Sieve Shaker, Model RX29 available from W.S. Tyler of Mentor, Ohio, or other similar shaking device at standard test conditions. After shaking is complete, the stimulation material retained on each sieve is removed and the weight is measured and recorded. The percentage of particles retained on each sieve is calculated by dividing the weights of the particles retained on each sieve by the initial sample weight.

Thickness Test

The thickness value of a selected portion or section of an article is determined using a thickness tester such as seen in FIG. 23. The thickness tester 2310 includes a granite base 2320 having a clamp shaft 2330 where the top surface 2322 of the granite base 2320 is flat and smooth. A suitable granite base is a Starret Granite Base, model 653G (available from The L.S. Starrett Company, having a place of business located in Athol, Mass., U.S.A.) or equivalent. A clamp arm 2340 is secured to the clamp shaft 2330 at one end 2342 of the clamp arm 2340, and a digital indicator 2350 is secured to the clamp arm 2340 at the opposing end 2344. A suitable indicator is a Mitutoyo ID-H Series 543 Digimatic Indicator (available from Mitutoyo America Corp., having a place of business located in Aurora, Ill., U.S.A.) or equivalent. Extending downward from the indicator 2350 is a vertically-movable plunger 2360.

To perform the procedure, a block 2370 having a length of 50 mm and a width of 44 mm is placed onto the granite base 2320. The block 2370 is constructed of acrylic and is flat and smooth on at least the bottom surface 2372. The thickness and weight of the block 2370 is configured such that the thickness tester 2310 provides a pressure to the sample of 0.69 kPa (0.1 psi). Next, the thickness tester 2310 is gently lowered such that the bottom surface 2362 of the plunger 2360 is in direct contact with the top surface 2374 of the block 2370 at the longitudinal 1 and transverse 2 center of the block 2370, and the plunger length is shortened by about 50%. The digital indicator 2350 is then tared (or zeroed) by pressing the "zero" button 2357. The digital display 2355 of the digital indicator 2350 should display "0.00 mm" or equivalent. The thickness tester 2310 is then raised and the block 2370 is removed. The test sample is then placed onto the top surface 2322 of the granite base 2320 and the block 2370 is gently placed on top of the test sample such that the block 2370 is substantially centered longitudinally 1 and transversely 2 on the sample. The thickness tester 2310 is then gently lowered again onto the block 2370 such that the bottom surface 2362 of the plunger 2360 is in direct contact with the top surface 2374 of the block 2370 at the longitudinal 1 and transverse 2 center of the block 2370, and the plunger length is shortened by about 50%, to provide a pressure of 0.69 kPa (0.1 psi). After 3 seconds, the measurement from the digital display 2355 is recorded to the nearest 0.01 mm.

DEFINITIONS

It should be noted that, when employed in the present disclosure, the terms "comprises," "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices which can absorb and contain fluids. For example, personal care absorbent articles refer to devices which are placed against or near the skin to absorb and contain the various fluids discharged from the body.

The term "attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements.

The term "bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements.

The term "coform" refers to a blend of meltblown fibers and absorbent fibers such as cellulosic fibers that can be formed by air forming a meltblown polymer material while simultaneously blowing air-suspended fibers into the stream of meltblown fibers. The coform material may also include other materials, such as superabsorbent materials. The meltblown fibers and absorbent fibers are collected on a forming surface, such as provided by a foraminous belt. The forming surface may include a gas-pervious material that has been placed onto the forming surface. Exemplary coform processes are described in U.S. Pat. No. 4,100,324 to Anderson et al.; U.S. Pat. No. 4,587,154 to Hotchkiss et al.; U.S. Pat. No. 4,604,313 to McFarland et al.; U.S. Pat. No. 4,655,757 to McFarland et al.; U.S. Pat. No. 4,724,114 to McFarland et al.; U.S. Pat. No. 4,100,324 to Anderson et al.; and U.K. Patent GB 2,151,272 to Minto et al., each of which is incorporated herein by reference in a manner that is consistent herewith.

The term "complex liquid" describes a liquid generally characterized as being a viscoelastic liquid pertaining primarily to aqueous liquids associated with menstruation.

The term "connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements.

The term "disposable" is used herein to describe absorbent articles that are not intended to be laundered or otherwise restored or reused as an absorbent article after a single use.

The terms "disposed on," "disposed along," "disposed with," or "disposed toward" and variations thereof are intended to mean that one element can be integral with another element, or that one element can be a separate structure bonded to or placed with or placed near another element.

The terms "elastic," "elasticized," "elasticity," and "elastomeric" and derivatives thereof mean that property of a material or composite by virtue of which it tends to recover its original size and shape after removal of a force causing a deformation. Suitably, an elastic material or composite can be elongated by at least 50 percent of its relaxed length and will recover, upon release of the applied force, at least 40 percent of its elongation.

The term "extensible" refers to a material or composite which is capable of extension or deformation without breaking, but does not substantially recover its original size and shape after removal of a force causing the extension or deformation (i.e., less than 40 percent recovery). Suitably, an extensible material or composite can be elongated by at least 50 percent of its relaxed length.

The term "fiber" refers to a continuous or discontinuous member having a high ratio of length to diameter or width. Thus, a fiber may be a filament, a thread, a strand, a yarn, or any other member or combination of these members.

The term "health/medical absorbent articles" includes a variety of professional and consumer health-care products including, but not limited to, products for applying hot or cold therapy, medical gowns (i.e., protective and/or surgical gowns), surgical drapes, caps, gloves, face masks, bandages, wound dressings, wipes, covers, containers, filters, disposable garments and bed pads, medical absorbent garments, underpads, and the like.

The term "household/industrial absorbent articles" includes construction and packaging supplies, products for cleaning and disinfecting, wipes, covers, filters, towels, disposable cutting sheets, bath tissue, facial tissue, nonwoven roll goods, home-comfort products including pillows, pads, mats, cushions, masks and body care products such as products used to cleanse or treat the skin, laboratory coats, coveralls, trash bags, pet care absorbent liners, laundry soil/ink absorbers, and the like.

The term "hydrophilic" describes materials which are wetted by aqueous liquids in contact with the materials. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, materials having contact angles less than 90 degrees are designated "wettable" or hydrophilic, and fibers having contact angles greater than 90 degrees are designated "nonwettable" or "hydrophobic".

The term "join" and its derivatives refer to the connecting, adhering, bonding, attaching, sewing together, or the like, of two elements. Two elements will be considered to be joined together when they are integral with one another or joined directly to one another or indirectly to one another, such as when each is directly joined to intermediate elements.

The term "liquid impermeable," when used in describing a layer or multi-layer laminate, means that liquid, such as urine, menses or bowel movement, will not pass through the layer or laminate, under ordinary use conditions, in a direction generally perpendicular to the plane of the layer or laminate at the point of liquid contact.

The term "liquid permeable" refers to any material that is not liquid impermeable.

The term "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. In the particular case of a coform process, the meltblown fiber stream intersects with one or more material streams that are introduced from a different direction. Thereafter, the meltblown fibers and other optional materials are carried by the high velocity gas stream and are deposited on a collecting surface. The distribution and orientation of the meltblown fibers within the formed web is dependent on the geometry and process conditions. Exemplary meltblown processes are described in various patents and publications, including NRL Report 4364, "Manufacture of Super-Fine Organic Fibers" by V. A. Wendt, E. L. Boone and C. D. Fluharty; NRL Report 5265, "An Improved Device For the Formation of Super-Fine Thermoplastic Fibers" by K. D. Lawrence, R. T. Lukas and J. A. Young; and U.S. Pat. No. 3,849,241 to Butin et al. and U.S. Pat. No. 5,350,624 to Georger et al., each of which is incorporated herein by reference in a manner that is consistent herewith.

The terms "nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblown processes, spunbond processes, air laying processes, wet layering processes and bonded-carded-web processes.

The term "personal care absorbent articles" includes, but is not limited to, absorbent articles such as diapers, diaper pants, baby wipes, training pants, absorbent underpants, child care pants, swimwear, and other disposable garments; feminine care products including sanitary napkins, wipes, menstrual pads, menstrual pants, panty liners, panty shields, interlabials, tampons, and tampon applicators; adult-care products including wipes, pads such as breast pads, containers, incontinence products, and urinary shields; clothing components; bibs; athletic and recreation products; and the like.

The term "sports/construction absorbent articles" includes headbands, wrist bands and other aids for absorption of perspiration, absorptive windings for grips and handles of sports equipment, and towels or absorbent wipes for cleaning and drying off equipment during use.

The terms "spunbond" and "spunbonded fiber" refer to fibers which are formed by extruding filaments of molten thermoplastic material from a plurality of fine, usually circular, capillaries of a spinneret, and then rapidly reducing the diameter of the extruded filaments.

The term "% by weight," "weight %," "wt %" or derivative therof, when used herein, is to be interpreted as based on the dry weight, unless otherwise specified.

These terms may be defined with additional language in the remaining portions of the specification.

DETAILED DESCRIPTION

As described above, one problem with previous articles incorporating a stimulation material is that when insulted by an aqueous liquid, the effect of the stimulation material tends to be relatively short. In other words, when utilizing stimulation materials without more, the stimulating effect begins immediately upon liquid insult and its efficacy is diminished rapidly, often prior to the end of the first liquid insult of the article, such as within the first minute. As a result, the effectiveness of signaling the wearer is less than desired. In addition, in some cases, excessive quantities of expensive stimulation material must be used in an attempt to extend the stimulating effect, which results in high manufacturing costs. Surprisingly, it has been discovered that incorporating the stimulation material in separate layers to form a laminated signal composite can extend the time scale for the stimulation effect. In addition, the unique structure of the signal composite of the present invention can provide the capability of having multiple stimulation effects over a sustained period after at least one insult, secure the stimulation material to reduce or prevent movement of the material, and can further provide the capability of changing the stimulation effect after at least one insult, as well as providing additional benefits to the user.

The improved stimulation device of this invention (hereinafter referred to as a "signal composite") is useful in disposable absorbent articles. An absorbent article of the present invention generally can have an absorbent core, and can optionally include a topsheet and/or a backsheet, where the absorbent core can be disposed between the topsheet and the backsheet. The signal composite comprises a carrier substrate layer, at least two stimulation layers, and at least two thermoplastic adhesive layers. In some aspects, the signal composite can further include an optional top porous-substrate layer disposed on the top surface of the signal composite.

To gain a better understanding of the present invention, attention is directed to FIGS. 1, 2, 4 and 5 for exemplary purposes showing a training pant and a signal composite of the present invention. It is understood that the present invention can also be suitable for use with various other disposable absorbent articles, including but not limited to other personal care absorbent articles, health/medical absorbent articles, household/industrial absorbent articles, sports/construction absorbent articles, and the like, without departing from the scope of the present invention.

Various materials and methods for constructing training pants are disclosed in U.S. Pat. No. 6,761,711 to Fletcher et al.; U.S. Pat. No. 4,940,464 to Van Gompel et al.; U.S. Pat. No. 5,766,389 to Brandon et al., and U.S. Pat. No. 6,645,190 to Olson et al., each of which is incorporated herein by reference in a manner that is consistent herewith.

Figure 2:
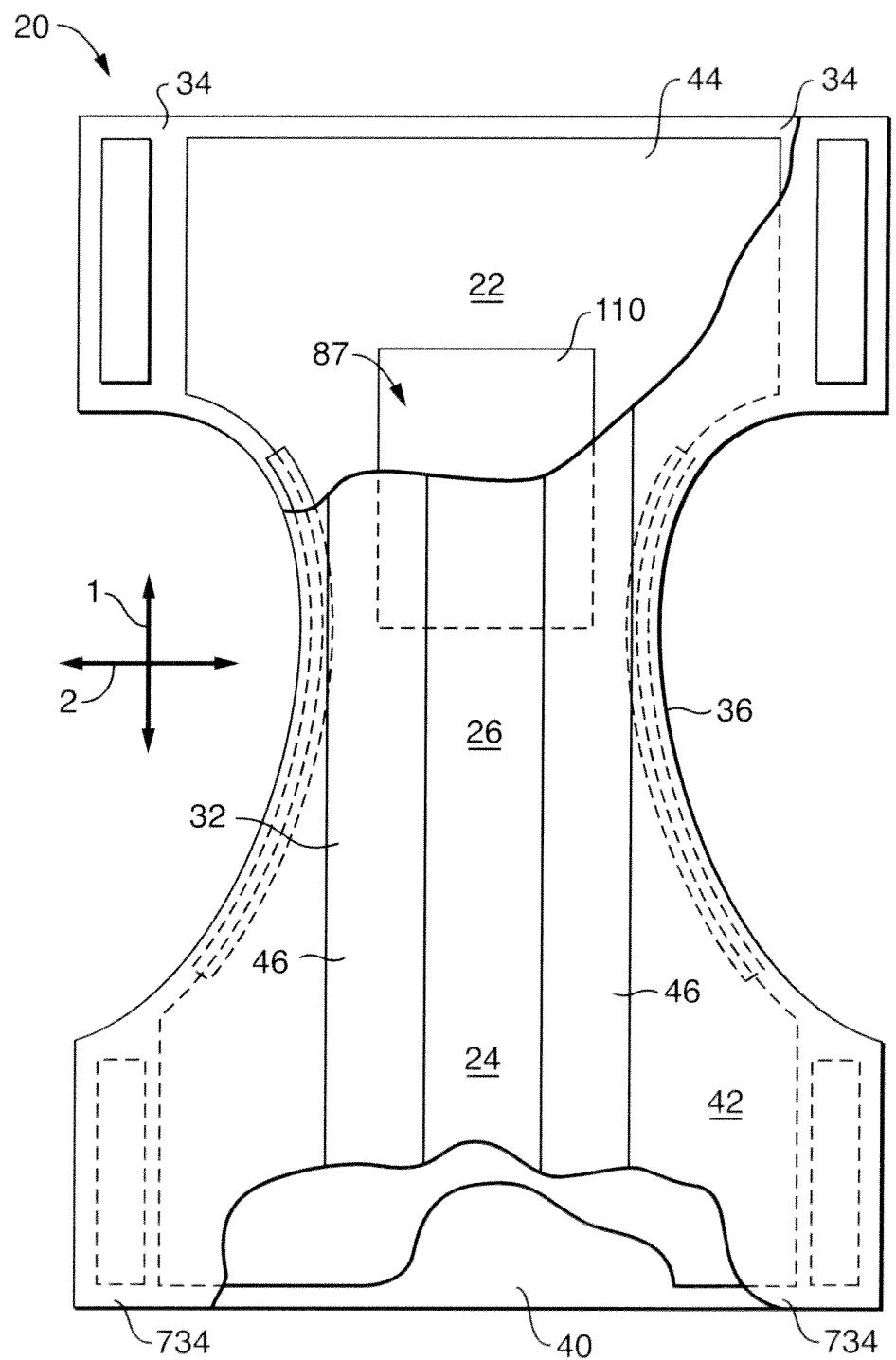

FIG. 1 illustrates a training pant 20 in a partially fastened condition, and FIG. 2 illustrates a training pant 20 in an opened and unfolded state. The training pant 20 defines a longitudinal direction 1 that extends from the front of the training pant when worn to the back of the training pant. Perpendicular to the longitudinal direction 1 is a lateral direction 2.

The training pant 20 defines a front region 22, a back region 24, and a crotch region 26 extending longitudinally between and interconnecting the front and back regions. The pant 20 also defines an inner surface (i.e., body-facing surface) adapted in use (e.g., positioned relative to the other components of the pant) to be disposed toward the wearer, and an outer surface (i.e., garment-facing surface) opposite the inner surface. The training pant 20 has a pair of laterally opposite side edges and a pair of longitudinally opposite waist edges.

The illustrated pant 20 may include a chassis 32, a pair of laterally opposite front side panels 34 extending laterally outward at the front region 22 and a pair of laterally opposite back side panels 734 extending laterally outward at the back region 24.

The chassis 32 includes a backsheet 40 and a topsheet 42 that may be joined to the backsheet 40 in a superimposed relation therewith by adhesives, ultrasonic bonds, thermal bonds or other conventional techniques. The chassis 32 may further include an absorbent core 44 such as shown in FIG. 2 disposed between the backsheet 40 and the topsheet 42 for absorbing fluid body exudates exuded by the wearer, and may further include a pair of containment flaps 46 secured to the topsheet 42 or the absorbent core 44 for inhibiting the lateral flow of body exudates.

The backsheet 40, the topsheet 42 and the absorbent core 44 may be made from many different materials known to those skilled in the art. All three layers, for instance, may be extensible and/or elastically extensible. Further, the stretch properties of each layer may vary in order to control the overall stretch properties of the product.

The backsheet 40, for instance, may be breathable and/or may be fluid impermeable. The backsheet 40 may be constructed of a single layer, multiple layers, laminates, spunbond fabrics, films, meltblown fabrics, elastic netting, microporous webs or bonded-carded-webs. The backsheet 40, for instance, can be a single layer of a fluid impermeable material, or alternatively can be a multi-layered laminate structure in which at least one of the layers is fluid impermeable.

The backsheet 40 can be biaxially extensible and optionally biaxially elastic. Elastic non-woven laminate webs that can be used as the backsheet 40 include a non-woven material joined to one or more gatherable non-woven webs or films. Stretch bonded laminates (SBL) and neck bonded laminates (NBL) are examples of elastomeric composites.

Examples of suitable nonwoven materials are spunbond-meltblown fabrics, spunbond-meltblown-spunbond fabrics, spunbond fabrics, or laminates of such fabrics with films, or other nonwoven webs. Elastomeric materials may include cast or blown films, meltblown fabrics or spunbond fabrics composed of polyethylene, polypropylene, or polyolefin elastomers, as well as combinations thereof. The elastomeric materials may include PEBAX elastomer (available from AtoFina Chemicals, Inc., a business having offices located in Philadelphia, Pa. U.S.A.), HYTREL elastomeric polyester (available from Invista, a business having offices located in Wichita, Kans. U.S.A.), KRATON elastomer (available from Kraton Polymers, a business having offices located in Houston, Tex., U.S.A.), or strands of LYCRA elastomer (available from Invista), or the like, as well as combinations thereof. The backsheet 40 may include materials that have elastomeric properties through a mechanical process, printing process, heating process or chemical treatment. For example, such materials may be apertured, creped, neck-stretched, heat activated, embossed, and micro-strained, and may be in the form of films, webs, and laminates.

One example of a suitable material for a biaxially stretchable backsheet 40 is a breathable elastic film/nonwoven laminate, such as described in U.S. Pat. No. 5,883,028, to Morman et al., incorporated herein by reference in a manner that is consistent herewith. Examples of materials having two-way stretchability and retractability are disclosed in U.S. Pat. No. 5,116,662 to Morman and U.S. Pat. No. 5,114,781 to Morman, each of which is incorporated herein by reference in a manner that is consistent herewith. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations. The topsheet 42 is suitably compliant, soft-feeling and non-irritating to the wearer's skin. The topsheet 42 is also sufficiently liquid permeable to permit liquid body exudates to readily penetrate through its thickness to the absorbent core 44. A suitable topsheet 42 may be manufactured from a wide selection of web materials, such as porous foams, reticulated foams, apertured plastic films, woven and non-woven webs, or a combination of any such materials. For example, the topsheet 42 may include a meltblown web, a spunbonded web, or a bonded-carded-web composed of natural fibers, synthetic fibers or combinations thereof. The topsheet 42 may be composed of a substantially hydrophobic material, and the hydrophobic material may optionally be treated with a surfactant or otherwise processed to impart a desired level of wettability and hydrophilicity.

The topsheet 42 may also be extensible and/or elastomerically extensible. Suitable elastomeric materials for construction of the topsheet 42 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon, a business having offices located in Cleveland, Ohio U.S.A.), or PEBAX elastomers. The topsheet 42 can also be made from extensible materials such as those described in U.S. Pat. No. 6,552,245 to Roessler et al. which is incorporated herein by reference in a manner that is consistent herewith. The topsheet 42 can also be made from biaxially stretchable materials as described in U.S. Pat. No. 6,969,378 to Vukos et al. which is incorporated herein by reference in a manner that is consistent herewith.

The article 20 can optionally further include a surge management layer which may be located adjacent the absorbent core 44 and attached to various components in the article 20 such as the absorbent core 44 or the topsheet 42 by methods known in the art, such as by using an adhesive. In general, a surge management layer helps to quickly acquire and diffuse surges or gushes of liquid that may be rapidly introduced into the absorbent structure of the article. The surge management layer can temporarily store the liquid prior to releasing it into the storage or retention portions of the absorbent core 44. Examples of suitable surge management layers are described in U.S. Pat. No. 5,486,166 to Bishop et al.; U.S. Pat. No. 5,490,846 to Ellis et al.; and U.S. Pat. No. 5,820,973 to Dodge et al., each of which is incorporated herein by reference in a manner that is consistent herewith.

The article 20 can further comprise an absorbent core 44. The absorbent core 44 may have any of a number of shapes. For example, it may have a 2-dimensional or 3-dimensional configuration, and may be rectangular shaped, triangular shaped, oval shaped, race-track shaped, I-shaped, generally hourglass shaped, T-shaped and the like. It is often suitable for the absorbent core 44 to be narrower in the crotch portion 26 than in the rear 24 or front 22 portion(s). The absorbent core 44 can be attached in an absorbent article, such as to the backsheet 40 and/or the topsheet 42 for example, by bonding means known in the art, such as ultrasonic, pressure, adhesive, aperturing, heat, sewing thread or strand, autogenous or self-adhering, hook-and-loop, or any combination thereof.

The absorbent core 44 can be formed using methods known in the art. While not being limited to the specific method of manufacture, the absorbent core can utilize forming drum systems, for example, see U.S. Pat. No. 4,666,647 to Enloe et al., U.S. Pat. No. 4,761,258 to Enloe, U.S. Pat. No. 6,630,088 to Venturino et al., and U.S. Pat. No. 6,330,735 to Hahn et al., each of which is incorporated herein by reference in a manner that is consistent herewith. Examples of techniques which can introduce a selected quantity of optional superabsorbent particles into a forming chamber are described in U.S. Pat. No. 4,927,582 to Bryson and U.S. Pat. No. 6,416,697 to Venturino et al., each of which is incorporated herein by reference in a manner that is consistent herewith.

In some desirable aspects, the absorbent core includes cellulose fiber and/or synthetic fiber, such as meltblown fiber, for example. Thus, in some aspects, a meltblown process can be utilized, such as to form the absorbent core in a coform line. In some aspects, the absorbent core 44 can have a significant amount of stretchability. For example, the absorbent core 44 can comprise a matrix of fibers which includes an operative amount of elastomeric polymer fibers. Other methods known in the art can include attaching superabsorbent polymer particles to a stretchable film, utilizing a nonwoven substrate having cuts or slits in its structure, and the like.

The absorbent core 44 can additionally or alternatively include absorbent and/or superabsorbent material. Accordingly, the absorbent core 44 can comprise a quantity of superabsorbent material and optionally fluff contained within a matrix of fibers. In some aspects, the total amount of superabsorbent material in the absorbent core 44 can be at least about 10% by weight of the core, such as at least about 30%, or at least about 60% by weight or at least about 90%, or between about 10% and about 98% by weight of the core, or between about 30% to about 90% by weight of the core to provide improved benefits. Optionally, the amount of superabsorbent material can be at least about 95% by weight of the core, such as up to 100% by weight of the core. In other aspects, the amount of absorbent fiber of the present invention in the absorbent core 44 can be at least about 5% by weight of the core, such as at least about 30%, or at least about 50% by weight of the core, or between about 5% and 90%, such as between about 10% and 70% or between 10% and 50% by weight of the core. In still other aspects, the absorbent core 44 can optionally comprise about 35% or less by weight unmodified fluff, such as about 20% or less, or 10% or less by weight unmodified fluff.

It should be understood that the absorbent core 44 is not restricted to use with superabsorbent material and optionally fluff. In some aspects, the absorbent core 44 may additionally include materials such as surfactants, ion exchange resin particles, moisturizers, emollients, perfumes, fluid modifiers, odor control additives, and the like, and combinations thereof. In addition, the absorbent core 44 can include a foam.

Figure 3:
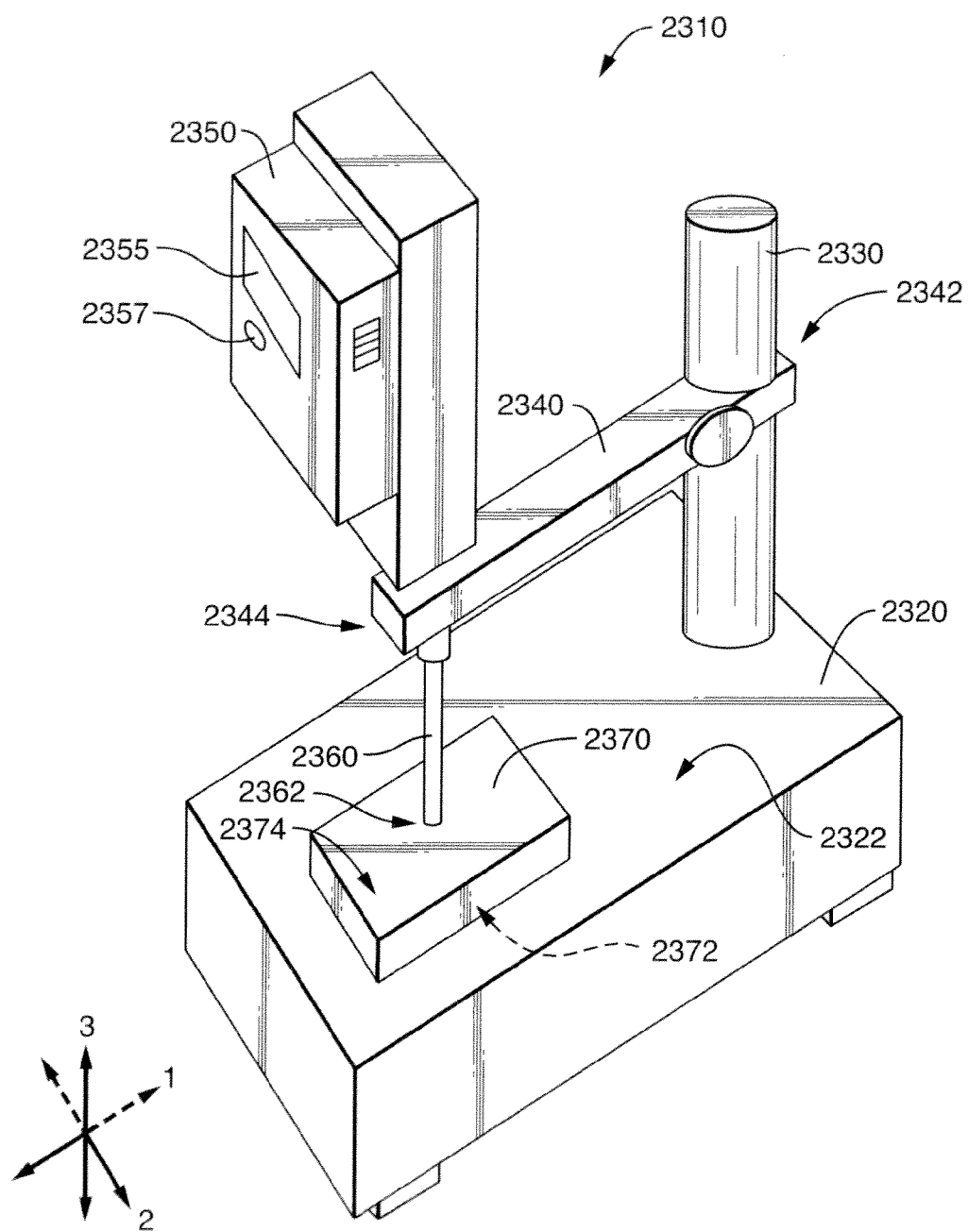
FIG. 3 is a perspective view of a thickness tester utilized in the Thickness Test.
Figure 4:
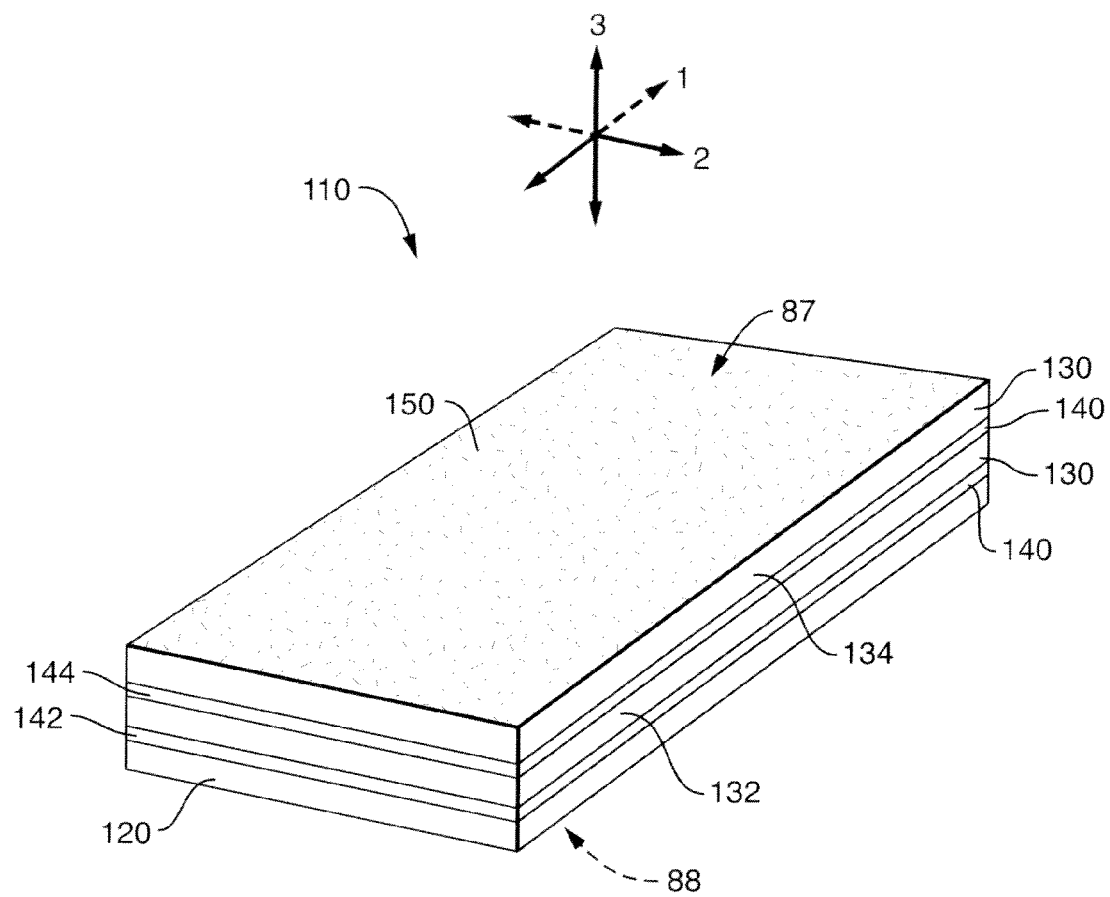
FIG. 4 is a perspective view of one embodiment of a signal composite of the present invention.

The disposable absorbent article 20 of the present invention also includes a signal composite 110 that is positioned and adapted to create a distinct physical sensation as the article 20 is insulted with an aqueous liquid. The signal composite 110 can have a longitudinal-direction 1 and a transverse-direction 2, which together can form a plane when in a laid-flat condition, hereinafter referred to as the "x-y plane." The signal composite also has a z-direction 3 that is perpendicular to the x-y plane. As seen in FIG. 3, the signal composite 110 can define a signal composite body-facing surface 87 intended to be disposed toward the wearer in use (i.e., an inner surface) and a signal composite garment-facing surface 88 intended to be disposed away from the wearer in use, opposite the member inner surface (i.e., an outer surface).

The signal composite 110 can have any desired shape. For example, it may have a 2-dimensional or 3-dimensional configuration, and may be rectangular shaped, triangular shaped, circular-shaped, oval shaped, race-track shaped, I-shaped, generally hourglass shaped, T-shaped and the like. In some aspects, the signal composite 110 can have no particular defined shape, but rather can have a random shape. Thus, the dimensions in at least the x-y plane can vary as desired. The signal composite 110 can also has a thickness dimension in the z-direction as desired. By way of example only, a suitable thickness of the signal composite 110 can be between 0.2 mm and 10 mm, such as between 0.25 mm and 5 mm or between 0.5 mm and 3 mm as measured by the Thickness Test. The signal composite 110 can also have a desired stiffness or flexibility. In some desirable aspects, the signal composite 110 will have approximately the same flexibility as the overall flexibility of the article 20.

Because the physical sensation resulting from the signal composite 110 is noticeable to the wearer, the wearer's ability to recognize when a liquid insult has occurred (and/or is occurring) will be enhanced. The signal composite 110 can be positioned within the article 20 in any operative location such that a user can detect a physical sensation as a result of the signal composite 110 receiving an aqueous liquid insult. For example, in some aspects, the signal composite 110 can be disposed adjacent to and in contact with the body-facing surface of an absorbent core 44. In other aspects, the signal composite 110 can be disposed adjacent to and in contact with the garment-facing surface and/or the body-facing surface of a topsheet 42. In still other exemplary aspects, the signal composite 110 can be disposed adjacent to and in contact with the body-facing surface or garment-facing surface of a surge layer, for example. Other configurations are also suitable for the invention as would be readily apparent to those skilled in the art.

The signal composite 110 of the present invention is a laminate comprising a carrier substrate layer 120. The carrier substrate layer 120 is provided by a separate web of material that can be at least partially or completely liquid permeable. Suitable liquid permeable materials include tissue layers; nonwovens such as meltblown, coform, spunbond, spunbond-meltblown-spunbond (SMS), bonded-carded-web (BCW), woven fabric; perforated films; foam layers; and the like. The carrier substrate layer can have a thickness of 0.1 mm to 5 mm, such as 0.1 mm to 3 mm, or 0.1 mm to 1 mm, as measured by the Thickness Test. Alternatively, the carrier substrate layer 120 can suitably have a basis weight of about 10 gsm to about 100 gsm, such as about 10 gsm to about 80 gsm, or about 10 gsm to about 50 gsm.

The signal composite 110 also comprises at least a first stimulation layer 132 and a second stimulation layer 134. Each stimulation layer 132,134 includes a stimulation material 150. The purpose of the stimulation material 150 is to provide the user with a perceptible sensation when a fluid insult is occurring and/or has occurred. The stimulation material 150 is desirably in the form of a solid, although gels and pastes are also within the scope of the invention. As it refers to stimulation materials, the term "solid" can include particles, flakes, fibers, agglomerates, granules, powders, spheres, pulverized materials, tablets or the like, as well as combinations thereof. The solids can have any desired shape such as, for example, cubic, rod-like, polyhedral, spherical or semispherical, rounded or semi-rounded, angular, irregular, and the like. Stimulation materials 150 for use in the disposable absorbent article 20 include those that dissolve in an aqueous liquid. The solubility of such stimulation materials 150 is desirably from about 0.1 to about 6 grams of material per gram of water (g/g), such as from about 0.1 g/g to about 3 g/g. In desirable aspects, at least two stimulation layers of the signal composite each comprise at least 50 wt % stimulation material that has a solubility of 0.1 grams to 6 grams of material per gram of water (g/g)

As can be appreciated, the signal composite 110 of the present invention can define a total amount of stimulation material 150, by weight. For example, in some aspects, each stimulation layer 130 can include 0.5 to 30 grams of stimulation material 150, such as 1 to 20 grams of stimulation material, or 1 to 10 grams of stimulation material. Alternatively, the amount of stimulation material 150 can be expressed in terms of basis weight. Accordingly, the basis weight of each stimulation layer 130 can range from about 20 grams/m$^2$ (gsm) to about 1000 gsm, such as about 25 gsm to about 500 gsm, or about 50 gsm to about 300 gsm.

In some aspects, each stimulation layer 132,134 can define a particle size distribution of stimulation material 150 within the signal composite 110. Accordingly, the stimulation material 150 particle size distribution of each layer 132,134 can be the same, or can be different. For example, each layer 132,134 can have a stimulation material 150 particle size distribution of between 90 microns and 710 microns, such as between 300 microns and 500 microns. In another example, the first stimulation layer 132 can have a stimulation material 150 particle size distribution of greater than 500 microns, such as between 500 and 710 microns, and the second stimulation layer 134 can have a stimulation material 150 particle size distribution of less than 500 microns, such as between 90 microns and 500 microns. It should be understood that in aspects where the stimulation material is in the form of particles, the invention is not limited to the exemplary stimulation material particle sizes presented above, but rather can include particles having sizes ranging from less than 90 microns (including nanoparticles) to greater than 710 microns, as measured by the Particle Size Test.

In general, the stimulation material 150 is responsive to contact with an aqueous solution such as urine, complex fluids or other aqueous body exudates to provide a stimulating effect, such as the absorption or release heat, expulsion of a gas or application of pressure to the user, for example. In general, the mechanism by which this is accomplished is by dissolution of the stimulation material 150 in the aqueous solution, by swelling of the material 150 in the aqueous solution, or by reaction of the material 150 in the aqueous solution. For example, the stimulation material 150 may include particles that have a substantial energy difference between a dissolved state and a crystalline state so that energy in the form of heat is absorbed or released to the environment upon contact with urine, complex fluids or other aqueous body exudates, or the stimulation material 150 may release or absorb energy during swelling or reacting in the aqueous solution. The selection of a particular stimulation material 150 and the determination of the amount to be used should be based in part on the desired stimulation effect.

In some aspects, the stimulation material 150 of the various aspects of the present invention can include a substance that provides a temperature change (referred to herein as a "temperature change agent") when placed near the wearer and contacted with an aqueous liquid. In some aspects, the temperature change can be an absorption or release of heat that is noticeable to the wearer. Absorption of heat by the temperature change agent (also referred to herein as a "cooling agent") will provide the wearer with a cool sensation, while a release of heat by the temperature change agent (also referred to herein as a "warming agent") will provide the wearer with a warm sensation. Reference is made to U.S. Patent Application Publication 2004/0254549 to Olson, et al., incorporated herein by reference in a manner that is consistent herewith, for additional information regarding the mechanism by which the temperature change sensation is accomplished. In some aspects, the cooling agents or warming agents can be provided in particulate form for ease of processing in the described embodiments. To illustrate, in aspects where the stimulation material 150 is a temperature change agent, the signal composite 110 may suitably provide a temperature change (i.e., cooler, warmer or both) when insulted with an aqueous liquid of at least about 2° C., such as at least about 5° C., or at least about 10° C., or between 3° C. and 15° C., for example.

In some aspects, the stimulation material 150 can include a temperature change agent in the form of a cooling agent, which can include those substances that absorb heat during dissolution from an insult. By way of example, polyols such as xylitol particles may be selected as cooling agents to provide a cooling sensation as xylitol particles absorb heat when dissolved in an aqueous liquid. Alternatively, other polyols such as sorbitol or erythritol may be advantageously selected to provide a cooling sensation. In yet other aspects, various combinations of the above stimulation materials 150 may be utilized. Suitable polyols can be obtained from Roquette America, Inc., a company having offices in Keokuk, Iowa, U.S.A., under the trade name of XYLIS ORB (xylitol) or NEOSORB (sorbitol). Such polyols can generally be obtained from the manufacturer in particular particle sizes, such as 90 microns, 300 microns, 500 microns, and the like for disposition in the stimulation layers 132,134.

Other suitable stimulation materials 150 that absorb heat during dissolution include salt hydrates, such as sodium acetate ($H_2O$), sodium carbonate ($H_2O$), sodium sulfate ($H_2O$), sodium thiosulfate ($H_2O$), and sodium phosphate ($H_2O$); anhydrous salts such as ammonium nitrate, potassium nitrate, ammonium chloride, potassium chloride, and sodium nitrate; organic compounds such as urea and the like or combinations thereof.

In some aspects, the stimulation material 150 can include a temperature change agent in the form of a warming agent, which can include those substances that release heat during dissolution from an insult. Examples of materials that release heat during dissolution include manganese chloride, aluminum chloride, aluminum sulfate, potassium aluminum sulfate, and the like or combinations thereof. In some aspects, the warming agent can also include those substances that release heat during swelling.

The stimulation material 150 can also include ortho esters or ketals such as menthone ketals that result from reacting menthone with alcohols containing 1 to 8 carbons or polyols containing 2 to 8 carbons, and all structural and optical isomers thereof. Particular menthone ketals that may be suitable include menthone-glycerol ketal and menthone-propylene glycol ketal. Other suitable ketals are disclosed in U.S. Pat. No. 5,348,750 to Greenberg and U.S. Pat. No. 5,266,592 to Grub et al., which are incorporated herein by reference in a manner that is consistent herewith.

The selection of a particular temperature change agent and the determination of the amount to be used should be based in part on the desired temperature change. For example, in some aspects, the total amount of stimulation material 150 present in the signal composite 110 can range from a basis weight of from about 40 gsm to about 3000 gsm, such as about 100 gsm to about 2000 gsm, or about 300 gsm to about 1000 gsm. In addition, as referenced above, in some aspects, the disposable absorbent article 20 desirably provides a surface temperature change when wet of from about 2° C. to 15° C. To achieve this result, the temperature change substance and the amount used should be selected so that the possible total energy change is from about 3 to about 30 calories per square centimeter (cal/cm$^2$), which may represent either a possible total energy release of from about 3 to about 30 cal/cm$^2$ or a possible total energy absorption of from about 3 to about 30 cal/cm$^2$, such as from about 6 to about 24 cal/cm$^2$, or about 12 to about 18 cal/cm$^2$.

Temperature change agents that absorb or release heat on contact with an aqueous solution desirably have a heat of solution, hydration, or reaction greater than about 30 cal/g, or less than about −30 cal/g. The heat of solution, hydration, or reaction is suitably within the range of from about 30 to about 90 cal/g or from about −30 to about −90 cal/g, such as from about 30 to about 70 cal/g or from about −30 to about −70 cal/g, such as xylitol at −32 cal/g or urea at −60 cal/g.

In some aspects, the stimulation material 150 can include a pressure change agent. Such a material can result in a pressure change expansion, foaming, fizzing, bubbling, gas release or other physical sensation such as where the user can feel a tingling sensation and/or hear a crackling sound, for example.

In some aspects, the signal composite 110 can be adapted to provide the wearer with an expanding or contracting dimensional change sensation. Dimensional change elements of this type are described in more detail in U.S. Pat. No. 5,649,914 to Glaug et al., which is incorporated herein by reference in a manner that is consistent herewith. A pressure change agent in the form of a dimensional change material includes materials that rapidly undergo a change in at least one dimension when exposed to an aqueous solution. The dimensional change is suitably either as an expansion to at least about 2 times a dry dimension or as a contraction to less than about one-half (½) of the dry dimension. For example, the dimensional change material can have a wet height dimension that is at least about 2 times greater than its dry height dimension, such as at least about 5 times greater for improved performance. The height dimension of the dimensional change material is in the z-direction 3 of the signal composite 110 so that the dimensional change is noticeable to the wearer of the absorbent article 20. In other aspects, the x-direction 1 and/or y-direction 2 of the signal composite 110 can additionally or alternatively remain the same, expand, or contract when exposed to an aqueous solution. Suitable materials for use in the dimensional change material include expandable foams, superabsorbents, or the like.

In some aspects, the pressure change agent produces a gas, such as carbon dioxide. Gas generating materials of this type are described in more detail in U.S. Pat. No. 7,002,055 to Long et al., which is incorporated herein by reference in a manner that is consistent herewith. The gas produced upon wetting with urine, complex fluids or other body exudates can produce a sound, a smell, a tingling sensation or apply pressure to the user.

In some aspects, the signal composite 110 can optionally include a surfactant. In some aspects, the gas producing materials can interact with the surfactant to produce a foam that applies pressure to the user. Thus, the surfactant component can be present as a foaming agent. For example, when a gas, such as carbon dioxide, is produced, the gas interacts with the surfactant and a bubble-filled foam is produced. These bubbles cause the article to swell and push against the skin of the wearer to alert the wearer of a liquid insult.

The surfactant used is not critical so long as it does not substantially irritate the skin upon contact, or adversely affect the efficacy of the stimulation material 150. A wide variety of surfactants may be suitable for use in accordance with the present invention. For example, suitable surfactants include anionic surfactants, nonionic surfactants, amphoteric surfactants, cationic surfactants, and combinations thereof. Examples of suitable anionic surfactants include alkyl benzene sulfonates, alkyl sulfates, alkyl ether sulfates, sulfosuccinates, and combinations thereof. Examples of suitable nonionic surfactants include ethoxylated alcohols, fatty acid alkanolamides, ethoxylated alkanolamides, amine oxides, and combinations thereof. Examples of suitable amphoteric surfactants include alkyl betaines, amidobetaines, and combinations thereof. Examples of suitable cationic surfactants include alkylammonium halides. In some aspects, the signal composite 110 can include from about 0.1 grams to about 15 grams of surfactant.

In other aspects, a pressure change agent in the form of a gas producing material can include an aqueous-soluble effervescent solid material. Such aqueous-soluble effervescent solid material typically comprises pressurized gas-containing cells. When the solid material having pressurized gas-containing cells is contacted with urine or other body exudates, the solid material begins to dissolve and the pressurized gas is released from the cells during dissolution of the solid material. In some aspects, this gas can interact with an optional surfactant and produce a foam and bubbles that cause the article 20 to press or apply pressure to the skin of the user.

In this aspect, the soluble effervescent solid material may include a sugar compound such as a mono-saccharide, disaccharide, or poly-saccharide that has been infused with a gas that is substantially non-reactive with human skin. Suitable gases for infusion into a solid material include, for example, carbon dioxide, air, nitrogen, argon, helium, other substantially inert gases, and combinations thereof. Specific examples of saccharides that can be used in accordance with the present disclosure include glucose, fructose, sucrose, lactose, maltose, dextrin, cyclodextrin, and the like, or combinations thereof. Also, a mixture of sucrose with corn syrup (containing glucose, maltose, and dextrin) can be used in accordance with this aspect of the present disclosure to produce a gas-containing effervescent material. Other examples of compounds that are capable of being prepared in such a manner as to trap pressurized gas in cells include, for example, water soluble compounds such as salts, alkali halides, and alkaline earth metal halides. Specific salts useful in the present disclosure include, for example, sodium chloride, potassium chloride, potassium bromide, lithium chloride, cesium chloride, and the like. In some aspects, the cells containing the pressurized gas have a diameter of from about 5 micrometers to about 100 micrometers.

A substantially non-reactive gas can be infused into the cells of the soluble solid material to produce an effervescent material useful in the present invention by first heating the starting material, such as a sugar, in a small amount of water until the material is dissolved. After dissolution of the material, the water is evaporated off leaving the material in a molten state. The molten material is then gasified by introducing a suitable gas, such as carbon dioxide, at a superatmospheric pressure into a sealed vessel containing the molten material. The molten material is agitated during gasification to ensure intimate contact between the molten material and the gas. Pressures of, for example, between about 50 psig (340 kPa) and about 1000 psig (6890 kPa) may be utilized to infuse the gas into the molten material. After gas infusion, the molten material is allowed to solidify while maintained in the sealed vessel to produce an effervescent material. A suitable procedure of producing a gas-containing solid material is set forth in U.S. Pat. No. 4,289,794 to Kleiner et al., which is incorporated herein by reference in a manner that is consistent herewith. The above procedure can produce solid effervescent materials containing cells of pressurized gas from about 50 psig (340 kPa) to about 900 psig (6200 kPa) which, when exposed to urine, complex fluids or other body exudates, allow the release of the trapped gas.

In some aspects, the pressure change agent comprising a gas producing material includes at least one acid and at least one base. The acid and base react together upon being wetted to produce a gas that may be, for example, carbon dioxide gas. The exact gas produced by the gas producing system is not critical, so long as the gas produced is substantially non-harmful to the skin of the wearer.

In some aspects, the stimulation material 150 can be a gas-generating material that includes a polymeric acid and a complementary base, resulting in an acid-base reaction. Suitable acidic polymers should be readily water soluble or water-wettable. Examples of suitable polymeric acids include, but are not limited to, polyacrylic acids, polystyrene phosphorus acids, and the like. In some aspects, the polymeric acid can be a "bidentate" or higher order acid. By "bidentate or higher order" it is meant that the polymeric acid has more than one acid group in its smallest polymer building block. This can be easily understood when one compares ascorbic acid to tartronic acid (two acid groups) and citric acid (three acid groups). In some aspects, the polymeric acids may be a dendrimer or the like where the dendrimer's surface and interior are fully functionalized with acid groups.

Other examples of suitable acids include, but are not limited to, acetic acid, lactic acid, amino acid, ascorbic acid, glyolic acid, salicylic acid, tartaric acid, citric acid, EDTA, tartronic acid, polyacrylic acid, maleic acid, phosphonic acid, and the like. Some non-limiting examples of polymeric acids are presented below:

Examples of simple polymeric acids include:

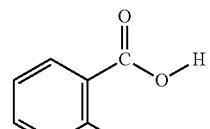

Salicyclic acid
FW: 138.123 g/mol

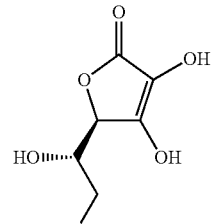

Vitamin C or
Ascorbic acid

Examples of dicarboxylic polymeric acids include:

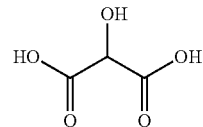

Tartronic acid

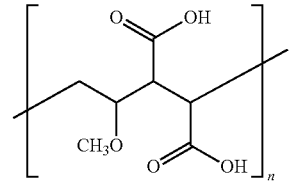

Poly(methyl vinyl ether-alt-
maleic acid) average
$M_w$ ~216,000 by LS,
average $M_n$ ~80,000, powder

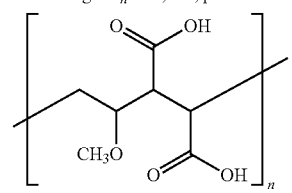

Poly(methyl vinyl ether-alt-
maleic acid) average
$M_w$ ~1,980,000 by LS,
average $M_n$ ~960,000, powder Examples of tricarboxylic polymeric acids include:

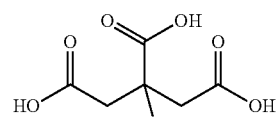

Citric acid

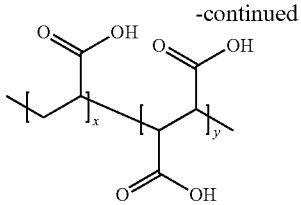

Poly(acrylic acid-co-maleic acid)
solution average $M_w$ 3,0000,
50 wt. % in $H_2O$ Examples of polyacrylic acids include:

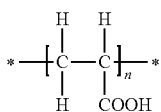

Poly(acrylic acid)
average Mw ~72
(monomer)

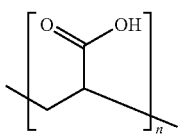

Poly(acrylic acid)
average $M_w$ ~1,800

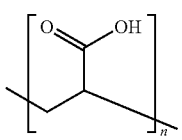

Poly(acrylic acid)
average $M_w$~450,000

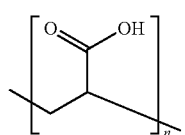

Poly(acrylic acid)
average $M_w$ ~1,250,000

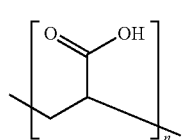

Poly(acrylic acid)
average $M_w$ ~3,000,000

An example of dendrimeric acids includes:

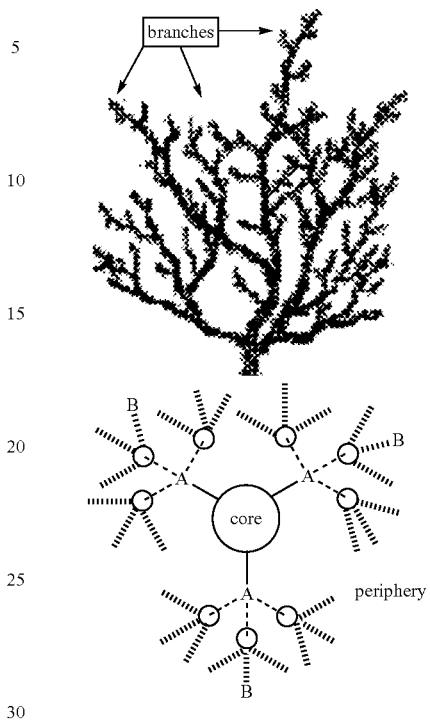

An example of strong polymeric acids includes:

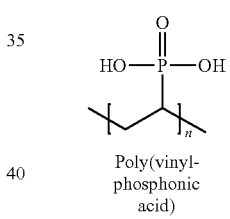

Poly(vinyl-
phosphonic
acid)

As referenced above, the acid-base reaction also includes a base, and can also include amphoteric substances that can react as either an acid or a base. For example, sodium bicarbonate (an amphoteric compound) has a pKa of 6.3 in water and causes aqueous solutions to be mildly alkaline. The reaction of sodium bicarbonate and an acid (e.g., acetic acid) results in a salt and carbonic acid, which readily decomposes to carbon dioxide and water.

In some aspects, it may be desirable to maximize the bicarbonate loading. For example, some non-limiting examples can include the following:

Tartaric acid and other cost effective dicarboxylic acids (two acidic groups)

Citric acid and other cost effective tricarboxylic acids (three acidic groups)

EDTA (four acidic groups)

Polymeric acids (may get equivalent two acidic groups like dicarboxylic acids)

In some aspects, it may be desirable to control the pH by molar ratios. To demonstrate, a non-limiting example of baking soda will be used. For purposes of example only, a complete reaction between baking soda and acids with a final pH of approximately 7 will be assumed (although it is understood that a slight excess of the base may be preferred for maximum carbon dioxide generation).

Baking soda:acid molar ratios
  1.05:1
  1.10:1
  1.25:1
Monodentate acid vs. baking soda
  1:1 ratio
Bidentate acid vs. baking soda
  1:1 ratio if only one acid group reacts
  0.5 (acid):1 ratio if two acid groups react
Tridentate acid vs. baking soda
  1:1 ratio if only one acid group reacts
  0.5 (acid):1 ratio if two acid groups react
  0.33 (acid):1 ratio if three acid groups react
Tetradentate acid vs. baking soda
  1:1 ratio if only one acid group reacts
  0.5 (acid):1 ratio if two acid groups react
  0.33 (acid):1 ratio if three acid groups react
  0.25 (acid):1 ratio if four acid groups react In some aspects, the stimulation material 150 can be encapsulated in an aqueous-soluble shell material prior to introduction into the signal composite 110. For example, if the signal composite 110 includes an acid and a base, the acid and the base may be separately encapsulated in a soluble encapsulation material to keep the components separated until wetted. Alternatively, the acid and base components may be encapsulated together if reactivity between the acid and the base in the absence of an aqueous liquid is not a concern. An optional surfactant can also be separately encapsulated, or may be encapsulated with the acid and/or the base in this example. It is understood that encapsulation may be used with other types of stimulation materials described herein.

The shell material used for encapsulation may be suitably constructed of a material such that it will release the encapsulated material upon contact with aqueous liquids such as urine, complex fluids or other body exudates. The aqueous liquids can cause the shell material to solubilize, disperse, swell, or disintegrate, or the shell material may be permeable such that it disintegrates or discharges the encapsulated material upon contact with the aqueous liquids. Suitable shell materials include cellulose-based polymeric materials (e.g., ethyl cellulose), carbohydrate-based materials (e.g., starches and sugars) and materials derived therefrom (e.g., dextrins and cyclodextrins) as well as other materials compatible with human tissues.

The shell thickness may vary depending upon the material encapsulated, and is generally manufactured to allow the encapsulated component to be covered by a thin layer of encapsulation material, which may be a monolayer or thicker laminate, or may be a composite layer. The layer should be thick enough to resist cracking or breaking of the shell during handling or shipping of the product or during wear which would result in breakage of the encapsulating material. The shell material should also be constructed such that humidity from atmospheric conditions during storage, shipment, or wear will not cause a breakdown of the microencapsulation layer.

In some aspects, at least one of the stimulation layers can further comprise a beneficial additive which provides an additional benefit to the user. Exemplary beneficial additives include surfactants, ion exchange resin particles, moisturizers, emollients, perfumes, fluid modifiers, odor control additives, pH buffering for the skin, vaginal health-care additives, coating materials for skin health, vitamins, medicines, and the like. However, for any given stimulation layer 130 of the present invention, at least 50 wt % of the material in the stimulation layer 130 should be stimulation material 150, such as 75 wt %, or more.

In addition to the carrier substrate layer 120 and the stimulation layers 130, the signal composite 110 also includes at least two thermoplastic adhesive layers 140. The purpose of the thermoplastic adhesive layers 140 is to help secure the stimulation materials 150 in the stimulation layers 130, and to generally hold the signal composite 110 together to form a laminated structure. For example, referring to FIGS. 4 and 5, a first thermoplastic layer 142 is disposed between the carrier substrate layer 120 and the first stimulation layer 132. In addition, a second thermoplastic adhesive layer 144 is disposed between the first stimulation layer 132 and the second stimulation layer 134.

Desirably, each thermoplastic adhesive layer 140 is strong enough to operably maintain the integrity of the signal composite 110 when the laminate is substantially dry. In addition, in some aspects, at least one thermoplastic adhesive layer 140 has sufficient strength to generally maintain the integrity of the laminate when the signal composite is insulted with an aqueous liquid. In some aspects, the holding strength of at least one thermoplastic adhesive layer 140, however, can be configured sufficiently low enough to substantially avoid excessive restriction of swelling, particularly when at least one of the stimulation layers 130 comprises a pressure change agent.

The thermoplastic adhesive layers 140 can each be the same, or can be different from one another. Materials that are suitable for forming the thermoplastic adhesive layers 140 include those that exhibit adhesive properties when transitioning from a molten state to a solid state. In some aspects, the adhesive composition is suitably a hot-melt adhesive. Such an adhesive generally comprises one or more polymers to provide cohesive strength, such as aliphatic polyolefins such as poly ethylene-co-propylene, polyamides, polyesters, and/or polyether blends; ethylene vinyl acetate copolymers; styrene-butadiene or styrene-isoprene block copolymers; and the like.

As an example, the hot-melt adhesive may contain from about 15 to about 50 weight percent cohesive strength polymer or polymers; from about 30 to about 65 weight percent resin or other tackifier or tackifiers; from more than zero to about 30 weight percent plasticizer or other viscosity modifier; and optionally less than about 1 weight percent stabilizer or other additive. It should be understood that other hot-melt adhesive formulations comprising different weight percentages of these components are possible. It is also contemplated that the adhesive composition may either be hydrophilic or hydrophobic without departing from the scope of this invention.

Examples of suitable materials include hydrophobic and hydrophilic hot melt polymers, such as those available from National Starch and Chemical Co. (having a place of business located in Bridgewater, N.J., U.S.A.) such as 34-5610, 34-447A, 70-3998 and 33-2058; those available from Bostik-Findley (having a place of business located in Milwaukee, Wis., U.S.A.) such as HX 4207-01, HX 2773-01, H2525A, H2800; and those available from H.B. Fuller Adhesives (having a place of business located in Saint Paul, Minn., U.S.A.) such as HL8151-XZP. Other adhesives are further described in U.S. Patent Publication No. 2005/0096623 to Sawyer, et al., which is incorporated herein by reference in a manner that is consistent herewith.

It is also contemplated that alternative adhesives may be used without departing from the scope of this invention. Examples of alternative adhesives include polyethylene oxide (PEO); polyethylene glycol (PEG); polyviny alcohol (PVOH); starch derivatives such as starch ethers, carboxymethyl starch, cationic starch, hydroxyalkyl starch, and the like, for example hydroxyethyl starch, hydroxypropyl starch and hydroxybutyl starch; cellulose derivatives such as cellulose ethers, hydroxyalkyl cellulose, for example hydroxyethyl cellulose, hydroxypropyl cellulose, methylcellulose, methyl propyl cellulose, carboxymethyl cellulose, and the like; polyacrylic acid; polyvinylmethyl ether; carrageenan; water-soluble alkyd resins; or the like, ethylene vinyl acetate copolymer (EVA) and combinations thereof. In addition, thermoplastic adhesive fibers, such as thermoplastic binder fibers, can also be used.

The thermoplastic adhesive layers 140 can each be applied by means well-known in the art. Exemplary means include, but are not limited to melt-blowing, spraying, slot-coating and the like. In some aspects, each thermoplastic adhesive layer 140 can have a thickness of about 0.01 mm to about 0.5 mm. Alternatively, the thermoplastic adhesive layers 140 can be expressed in terms of basis weight. Accordingly, the basis weight of each thermoplastic adhesive layer 140 can range from about 2 gsm to about 50 gsm, such as about 2 gsm to about 25 gsm. In still other aspects, the total amount of thermoplastic adhesive in the thermoplastic adhesive layers 140 can be about 2-15 wt % of the total weight of all stimulation layers 130 in the signal composite.

In some aspects, it may be desirable that the thermoplastic adhesive layers 140 are liquid permeable. However, in cases where the thermoplastic adhesive layers 140 are not liquid permeable, the layers can be made permeable by perforating the signal composite 110. Means for perforating materials are well-known in the art, and include, but are not limited to, needle-punch, air-jet, and the like. In other aspects, it may be desirable that the thermoplastic adhesive layers 140 are water-soluble.

Figure 5:
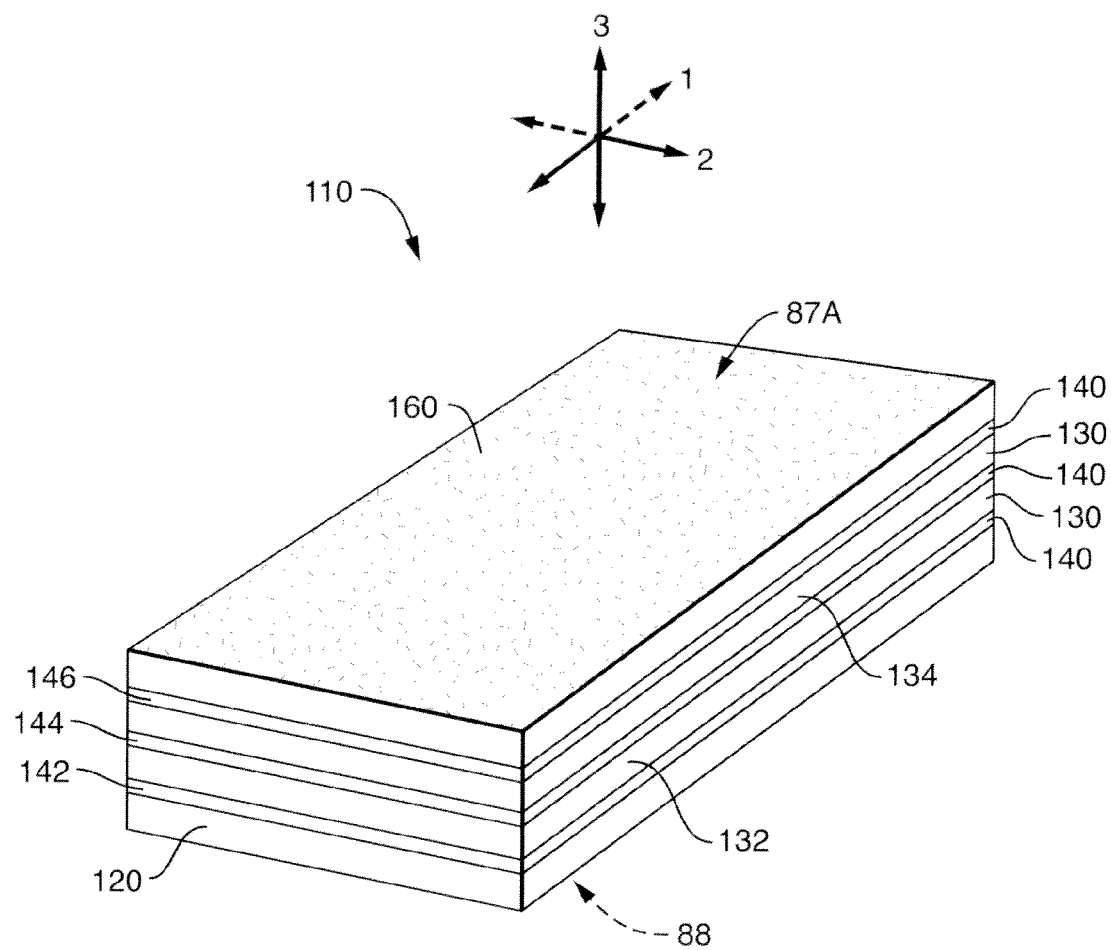
FIG. 5 is a perspective view of one embodiment of a signal composite of the present invention having an additional thermoplastic adhesive layer and an additional liquid-pervious substrate layer.

In some aspects, it may be desirable to further include an additional liquid pervious layer 160 to the body-facing surface 87 of the signal composite 110, such as seen in the exemplary embodiment of FIG. 5, thus forming a new body-facing surface 87A. The illustrated example comprises a carrier substrate layer 120, a first thermoplastic adhesive layer 142, a first stimulation layer 132, a second thermoplastic adhesive layer 144, a second stimulation layer 134, a third thermoplastic adhesive layer 146, and an additional liquid pervious layer 160. The additional liquid pervious layer 160 can be included for many reasons, including but not limited to reducing the abrasiveness of the body-facing surface of the signal composite 110, providing a means to include a printed graphic on the signal composite 110, or numerous other desires. Liquid permeable materials suitable for the additional liquid pervious layer 160 include tissue layers; nonwovens such as meltblown, coform, spunbond, spunbond-meltblown-spunbond (SMS), bonded-carded-web (BCW), woven fabric, perforated films, foam layers, and the like. The additional liquid pervious layer 160 can suitably have a basis weight of about 10 gsm to about 50 gsm, such as about 10 gsm to about 30 gsm, or about 10 gsm to about 20 gsm.

Figure 6:
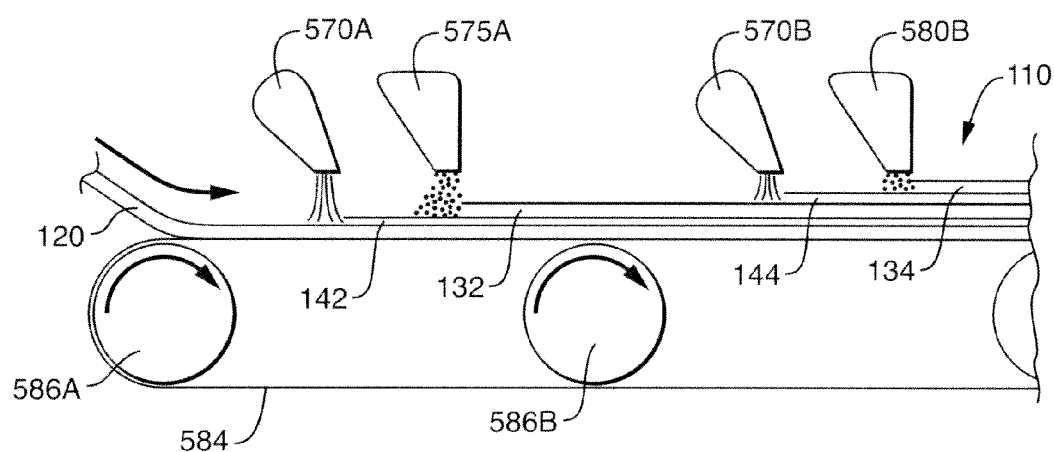
FIG. 6 illustrates an exemplary process for constructing the signal composite of the present invention.

Construction of the signal composite 110 of the present invention can be accomplished by any suitable method well-known to those skilled in the art. FIG. 6 illustrates one exemplary process for constructing the signal composite 110. A carrier substrate layer 120 is supported on a support belt 584. The support belt 584 is supported on two or more rolls 586A and 586B provided with suitable driving means (not shown) for moving the belt 584. The carrier substrate layer 120 passes under a first melt blown process 570A which applies a first thermoplastic adhesive layer 142 to the top surface of the carrier substrate layer 120. The composite then passes under a first gravimetric feeder 575A which deposits stimulation material 150 (and any other beneficial additives) to the top surface of the tacky first thermoplastic adhesive layer 142 to provide a first stimulation layer 132. The composite then passes under a second melt blown process 570B which applies a second thermoplastic adhesive layer 144 to the top surface of the first stimulation layer 132. The composite then passes under a second gravimetric feeder 575B which deposits stimulation material 150 (and any other beneficial additives) to the top surface of the tacky second thermoplastic adhesive layer 144 to provide a second stimulation layer 134, thus providing an exemplary signal composite 110 of the present invention. Other methods for constructing the laminated signal composite 110 will be readily apparent to those skilled in the art.

It is understood that signal composite 110 of the present invention is not limited to two stimulation layers 130. Rather, the signal composite can have any number of stimulation layers 130 as desired (with corresponding thermoplastic adhesive layers 140 disposed therebetween), provided that it has at least two stimulation layers, wherein the each stimulation layer comprises at least 50 wt % of stimulation material 150 having a solubility of from 0.1 grams to 6 grams of material per gram of water. For example, the signal composite 110 can comprise 2-15 stimulation layers 130, such as 2-10 or 2-5 stimulation layers for improved performance. For instance, for a signal composite having at least two stimulation layers and two thermoplastic adhesive layers, the signal composite can further comprise 1-13 additional stimulation layers, and 1-13 additional thermoplastic adhesive layers such that the additional thermoplastic adhesive layers and the additional stimulation layers are disposed in an alternating fashion. In addition, each layer of the signal composite 110 may or may not be coextensive with another layer in the longitudinal direction 1 and/or the transverse direction 2.

The signal composite 110 as illustrated in the figures is generally rectangular. However, as noted above, the signal composite can have any of a number of shapes. In some aspects, the signal composite can be attached in an absorbent article, such as to the absorbent core, a surge layer and/or a topsheet for example, by bonding means known in the art, such as ultrasonic, pressure, adhesive, aperturing, heat, sewing thread or strand, autogenous or self-adhering, or the like, and combinations thereof. In other aspects, the signal composite may be free-floating within the article. In addition, the signal composite 110 can be present in the article 20 as a single layer or as multiple layers, such as strips.

Figure 7:
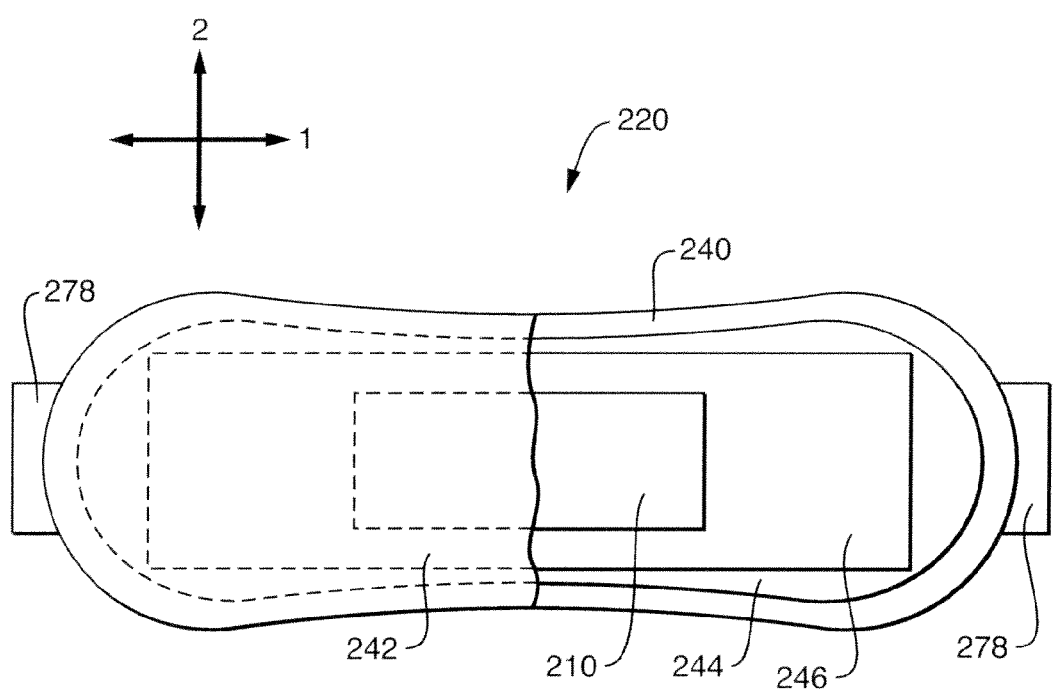
FIG. 7 is a feminine care pad having a signal composite of the present invention.

While a training pant has been described above for exemplary purposes, it is understood that the signal composite of the present invention can be suitable for other personal care absorbent articles. For example, FIG. 7 shows an absorbent article 220 in the form of a feminine care pad having a topsheet 242, a backsheet 240, an absorbent core 244, a surge layer 246 and a peel strip 278. The absorbent article 220 further comprises a separate signal composite 210 disposed between the topsheet 242 and the surge layer 246.

The present invention may be better understood with reference to the following examples.

EXAMPLES

Example 1

In this example, a signal composite was produced by first providing a spunbond-meltblown-spunbond carrier substrate layer comprising polypropylene (available from Kimberly-Clark Corporation, having a place of business in Neenah, Wis., U.S.A.) having a basis weight of 18 gsm. A first thermoplastic adhesive layer was applied to the entire top surface of the carrier substrate layer using first a meltblown process at 160° C. The first thermoplastic adhesive layer consisted of National Starch 34-5610 hot melt polymer (available from National Starch and Chemical Company, having a place of business located in Bridgewater, N.J., U.S.A.) and had a basis weight of 7 gsm. The meltblown process conditions were as follows:

Line Speed—15.2 meters/min
Die Angle (degrees from horizontal)≦75°
Forming Height (cm)—23 cm
Primary Air Pressure (kPa)—138 kPa
Polymer Melt Temperature—160° C.
Adhesive Polymer—National Starch 34-5610 hot melt Immediately after the first thermoplastic adhesive layer was applied to the carrier substrate layer (i.e., while the adhesive layer was still tacky), a layer of xylitol particles was applied to the entire top surface of the first adhesive layer using a CHRISTY Dry Material Dispensing Machine (available from Christy Machine Company, having a place of business in Fremont, Ohio, U.S.A.) located a distance of 30.5 cm in the machine direction from the first meltblown unit to form a first stimulation layer having a basis weight of 175 gsm.

A second thermoplastic adhesive layer consisting of National Starch 34-5610 hot melt polymer and having a basis weight of 7 gsm was applied to the top surface of the first stimulation layer using the same style meltblown unit and having the same process conditions as for the first thermoplastic adhesive layer. Immediately after the second thermoplastic adhesive layer was applied to the top surface of the first stimulation layer (i.e., while the adhesive layer was still tacky), a layer of xylitol particles was applied to the entire top surface of the second adhesive layer using a CHRISTY Dry Material Dispensing Machine located a distance of 30.5 cm in the machine direction from the second meltblown unit to form a second stimulation layer having a basis weight of 175 gsm.

A third thermoplastic adhesive layer consisting of National Starch 34-5610 hot melt polymer and having a basis weight of 7 gsm was applied using the same style meltblown unit and having the same process conditions as for the first thermoplastic adhesive layer. Immediately after the third thermoplastic adhesive layer was applied to the top surface of the second stimulation layer (i.e., while the adhesive layer was still tacky), a 16 gsm tissue substrate consisting of 100 wt % NB 416 (a bleached southern softwood Kraft pulp, available from Weyerhaeuser Co., having a place of business in Federal Way, Wash., U.S.A.) was applied to the entire top surface of the third adhesive layer, thus completing the signal composite.

Figure 8A:
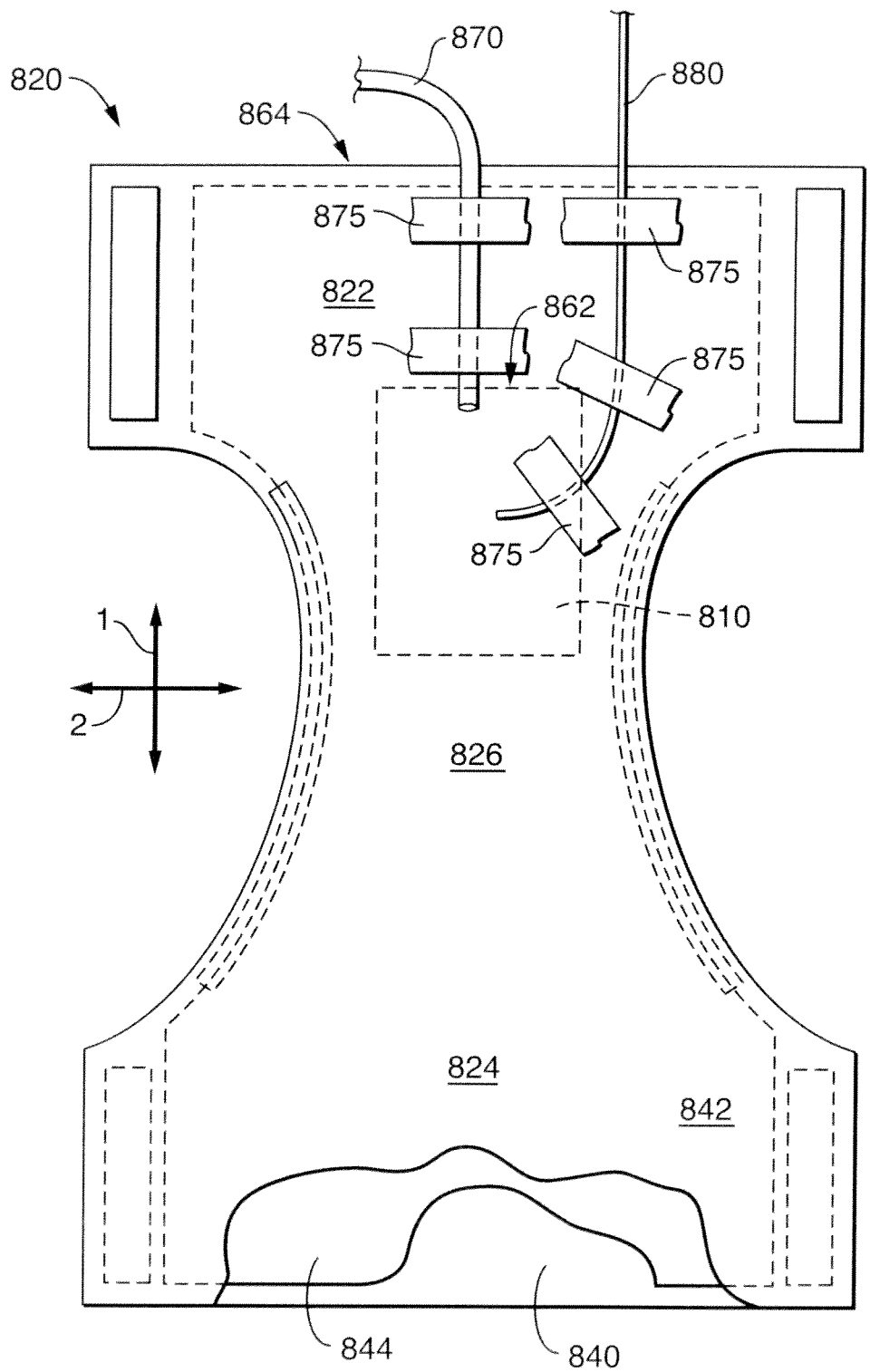
FIG. 8A is a plan view of a training pant in an unfastened, stretched and laid flat condition, showing the surface of the training pant that faces toward the wearer and having a signal composite, a flexible plastic tube and a thermocouple as configured for Examples 1 and 2.

With reference to FIG. 8A, a 7.6 cm by 7.6 cm sample was cut from the signal composite to form a signal composite sample 810, which was then placed between the absorbent core 844 and the topsheet 842 of a training pant 820 between the crotch region 826 and the front region 822. While FIG. 8A illustrates a training pant 820 in general, the actual training pant utilized for this example was a current size 2T-3T HUGGIES PULL-UPS training pant (available from Kimberly-Clark Corporation, having a place of business in Neenah, Wis., U.S.A.) Flexible plastic tubing 870 having a length of approximately 30 cm and an inner diameter by outer diameter of 3.2 mm×4 8 mm (available Catalog #89068-530 from VWR International, LLC, having a place of business located in West Chester, Pa., U.S.A.) was attached to the body-facing surface of the topsheet 842 using adhesive tape 875 such that one end of the tubing 870 was positioned approximately 25 mm below the top edge 862 of the signal composite sample 810 (as viewed through the topsheet 842), and from there extended upwards through the front region 822 and past the approximate transverse 2 center of the top edge 864 of the training pant 820. In addition, a flexible thermocouple 880 was also attached to the body-facing surface of the topsheet 842 using adhesive tape 875 such that the end of the thermocouple 880 was positioned at the approximate longitudinal 1 and transverse 2 center of the signal composite sample 810, and from there extended upwards through the front region 822 and past the top edge 864 of the training pant 820.

Figure 8B:
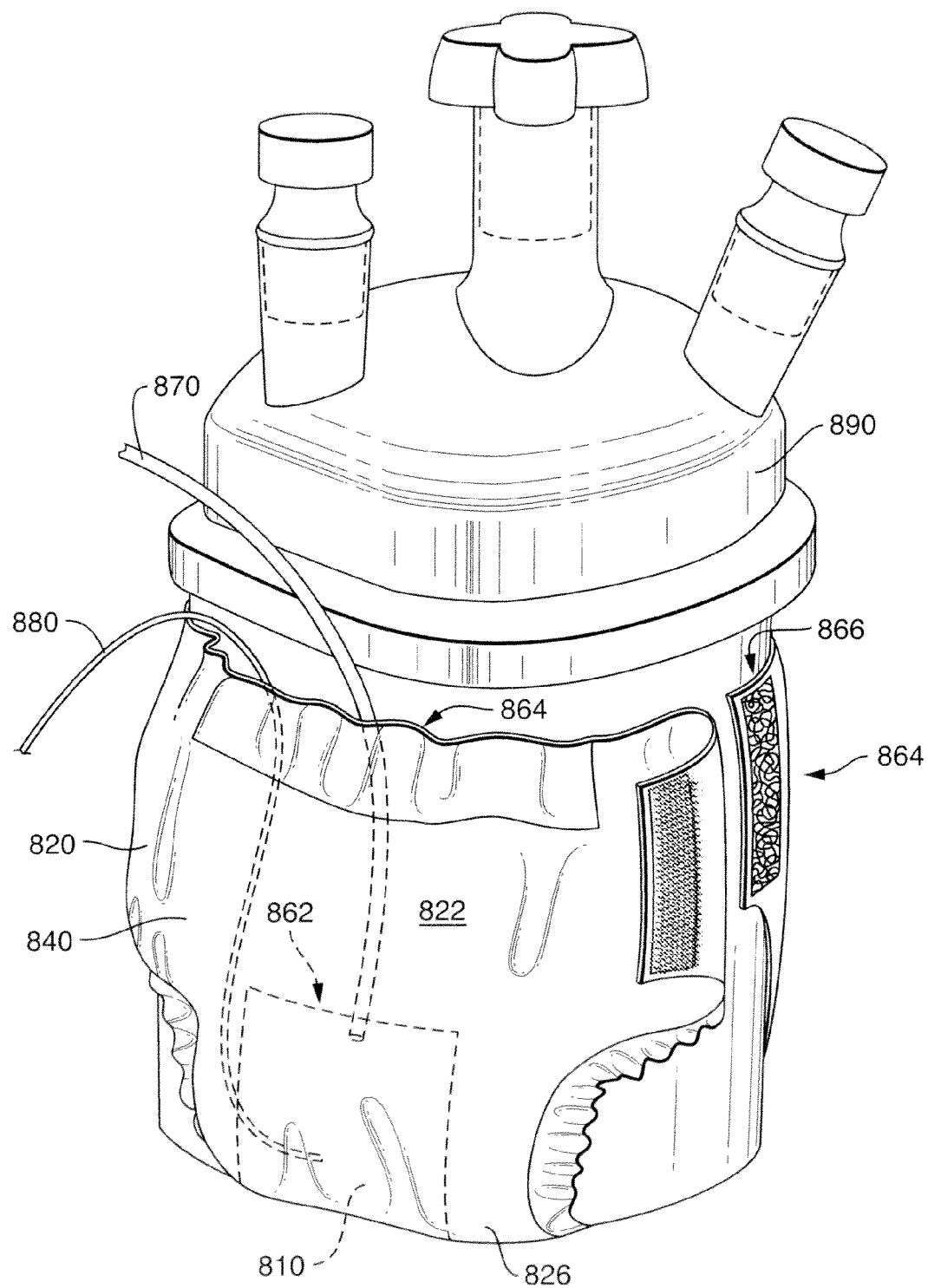
FIG. 8B is a perspective view of the training pant of FIG. 8A donned on a double jacketed flask for Examples 1 and 2.

With further reference to FIG. 8B, the modified training pant 820 was then fitted onto a 2000 ml double jacketed glass container 890 such that the crotch region 826 was located at the bottom of the glass container 890, and the front region 822 and the back region 824 were located around the sides of the flask 890. The flask 890 contained water in both chambers of the container 890 having a temperature of 37° C. at a level that extended past the top edges 864,866 of the training pant 820. The purpose of the container 890 with water was to simulate conditions of the training pant 820 and signal composite 810 being disposed against a user's body at constant body temperature. When the temperature of the training pant 820 reached equilibrium, as determined by the thermocouple 880, the temperature was recorded as the baseline temperature. Then, 50 ml of water at 37° C. was injected into the tubing 870 over an 8 second period using a syringe such that the water insulted the training pant 820 at the location of the signal composite 810. Using the thermocouple 880, the temperature of the training pant 820 at the location of the signal composite 810 was monitored for 5 minutes. The temperature at 5 minutes was then recorded. The temperature at 5 minutes was then subtracted from the baseline temperature, which resulted in a temperature change of −6.0° C.

The results of this example show that the signal composite of the present invention not only provides a significant cooling effect after aqueous insult, but also shows that the unique structure of the signal composite continues to provide a cooling effect even after 5 minutes after aqueous insult.

Example 2

In this example, a signal composite was produced in the same manner, using the same materials and the same process conditions as Example 1 above to form a signal composite sample 810. The flexible plastic tubing 870 and the flexible thermocouple 880 were also attached to training pant 820 in the same manner as Example 1 above. However, in this Example 2, the second stimulation layer having a basis weight of 172 gsm consisted of 75 wt % xylitol and 25 wt % FAVOR SXM 9500 superabsorbent material (available from Evonik Stockhausen, having a place of business in Greensboro, N.C., U.S.A.) rather than 100 wt % xylitol as in Example 1 above. In addition, prior to inserting the signal composite sample 810 of this Example 2 into the training pant 820 between the topsheet 842 and the absorbent core 842, the thickness (mm) of the signal composite sample 810 was measured using the Thickness Test, and the result was recorded as the baseline thickness.

The modified training pant 820 of this Example 2 was then fitted onto the double jacketed glass container 890 as in FIG. 8B such that the crotch region 826 was located at the bottom of the container 890, and the front region 822 and the back region 824 were located around the sides of the container 890. The container 890 again contained water in both chambers having a temperature of 37° C. at a level that extended past the top edges 864,866 of the training pant 820. When the temperature of the training pant 820 reached equilibrium, as determined by the thermocouple 880, the temperature was recorded as the baseline temperature. Then, 50 ml of water at 37° C. was injected into the tubing 870 over an 8 second period using a syringe such that the water insulted the training pant 820 at the location of the signal composite 810. Using the thermocouple 880, the temperature of the training pant 820 at the location of the signal composite 810 was monitored for 5 minutes. The temperature at 5 minutes was then recorded. The temperature at 5 minutes was then subtracted from the baseline temperature, which resulted in a temperature change of −6.5° C.

In addition, in this Example 2, the training pant 820 was immediately removed from the container 890 at the 5 minute point, the signal composite 810 was carefully extracted from the training pant 820, and the thickness (mm) of the signal composite 810 was immediately measured using the Thickness Test. The result was recorded as the thickness after insult. The baseline thickness was then subtracted from the thickness after insult to provide the thickness change, and the % Expansion in the z-direction was calculated using the following formula, resulting in a % Expansion of approximately 300% in the z-direction:

thickness change (mm)/baseline thickness (mm)× 100%=% Expansion

The results of this Example 2 show that the signal composite of the present invention not only provides a significant cooling effect after aqueous insult, but also shows that the unique structure of the signal composite continues to provide a cooling effect even after 5 minutes after aqueous insult. This example further demonstrates that the presence of 25 wt % superabsorbent in the second stimulation layer further extends the cooling effect time scale, as evidenced by an even greater change in temperature from the baseline temperature at 5 minutes after insult, as compared to Example 1. Moreover, the advantage of including an additional additive to the at least one of the stimulation layers of the signal composite, resulted in a pressure change effect, in addition to the cooling effect, as evidenced by a signal composite z-direction expansion of approximately 300%. In addition, the presence of at least 25 wt % superabsorbent in at least one of the stimulation layers can potentially help reduce leakage of the training pant by providing an additional absorption function prior to the absorbent core.

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the desirable embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:

1. An absorbent article comprising a signal composite;
   wherein the signal composite has a body-facing surface, a garment-facing surface, a longitudinal direction, a transverse direction and a z-direction;
   wherein the signal composite comprises a carrier substrate layer, a first stimulation layer, a second stimulation layer, a first thermoplastic adhesive layer and a second thermoplastic adhesive layer;
   wherein the carrier substrate layer is liquid permeable or water-soluble and is disposed as a bottom layer of the signal composite in the z-direction to provide the garment-facing surface of the signal composite;
   wherein the first stimulation layer comprises a first stimulation material and is disposed above the carrier substrate layer;
   wherein the second stimulation layer comprises a second stimulation material and is disposed above the first stimulation layer to provide the body-facing surface of the signal composite;
   wherein the first thermoplastic adhesive layer is liquid permeable or water-soluble and is disposed between and adjacent to the carrier substrate layer and the first stimulation layer;
   wherein the second thermoplastic adhesive layer is liquid permeable or water-soluble and is disposed between the first stimulation layer and the second stimulation layer; and
   wherein each stimulation layer comprises at least 50 wt % of stimulation material having a solubility of from 0.1 grams to 6 grams of material per gram of water.

2. The absorbent article of claim 1 wherein the carrier substrate layer has a basis weight of 10 gsm and 50 gsm.

3. The absorbent article of claim 1 wherein the carrier substrate layer has a thickness in the z-direction of 0.1 mm and 1 mm, as measured by the Thickness Test.

4. The absorbent article of claim 1 wherein the carrier substrate layer is a nonwoven substrate.

5. The absorbent article of claim 1 wherein the carrier substrate layer is a thermoplastic water-soluble polymer film.

6. The absorbent article of claim 1 wherein at least one of the first stimulation layer and the second stimulation layer comprises a stimulation material in the form of a cooling agent, wherein the cooling agent is selected from xylitol, sorbitol or urea.

7. The absorbent article of claim 1 wherein the first stimulation layer comprises stimulation material in the form of a cooling agent and the second stimulation layer comprises stimulation material in the form of a warming agent.

8. The absorbent article of claim 1 wherein the first stimulation layer comprises stimulation material in the form of a cooling agent, and the second stimulation layer comprises stimulation material in the form of a cooling agent and a pressure change agent.

9. The absorbent article of claim 1 wherein each of the first stimulation layer and the second stimulation layer has a basis weight of 25 gsm to 500 gsm.

10. The absorbent article of claim 1 wherein each of the first thermoplastic adhesive layer and the second thermoplastic adhesive layer is hydrophobic.

11. The absorbent article of claim 1 wherein each of the first thermoplastic adhesive layer and the second thermoplastic adhesive layer has a basis weight of 2 gsm to 25 gsm.

12. The absorbent article of claim 1 wherein at least one of the first stimulation layer and the second stimulation layer further comprises a beneficial additive selected from surfactants, ion exchange resin particles, moisturizers, emollients, perfumes, fluid modifiers, odor control additives, pH buffering for the skin, vaginal health-care additives, coating materials for skin health, vitamins and medicines.

13. The absorbent article of claim 1 wherein the signal composite has a thickness in the z-direction of 0.25 mm to 5 mm, as measured by the Thickness Test.

14. The absorbent article of claim 1 wherein each of the carrier substrate layer, first stimulation layer, second stimulation layer, first thermoplastic adhesive layer and second thermoplastic adhesive layer are coextensive in the longitudinal direction and in the transverse direction.

15. The absorbent article of claim 1, wherein the signal composite further comprises at least one additional stimulation layer and at least one additional thermoplastic adhesive layer, wherein the at least one additional stimulation layer is disposed above and adjacent the second stimulation layer, and wherein the at least one additional thermoplastic adhesive layer is liquid permeable or water-soluble and is disposed between and adjacent to the second stimulation layer and the at least one additional stimulation layer.

16. The absorbent article of claim 15, wherein the signal composite further comprises 1-13 additional stimulation layers, and 1-13 additional thermoplastic adhesive layers such that the additional thermoplastic adhesive layers and the additional stimulation layers are disposed in an alternating fashion.

17. The absorbent article of claim 1, wherein the signal composite further comprises an additional liquid-pervious substrate layer and an additional thermoplastic adhesive layer, wherein the additional liquid-pervious substrate layer is disposed above the second stimulation layer, and wherein the additional thermoplastic adhesive layer is liquid permeable or water-soluble and is disposed between and adjacent to the second stimulation layer and the additional liquid-pervious stimulation layer.

18. An absorbent article comprising a signal composite;
   wherein the signal composite has a body-facing surface, a garment-facing surface, a longitudinal direction, a transverse direction and a z-direction;
   wherein the signal composite comprises a carrier substrate layer, 2-15 stimulation layers, and 2-15 thermoplastic adhesive layers;
   wherein the carrier substrate layer is liquid permeable or water-soluble and is disposed as a bottom layer of the signal composite in the z-direction to provide the garment-facing surface;
   wherein the stimulation layers each comprise stimulation materials and are each disposed above the carrier substrate layer;
   wherein one of the stimulation layers is disposed as a top layer of the signal composite in the z-direction to provide the body-facing surface;
   wherein each thermoplastic adhesive layer is liquid permeable or water-soluble;
   wherein one of the thermoplastic adhesive layers is disposed between and adjacent to the carrier substrate layer and one of the stimulation layers, and each of the remaining thermoplastic adhesive layers is disposed between and adjacent to the remaining stimulation layers in an alternating fashion;
   wherein at least 50 wt % of the stimulation materials in at least two stimulation layers have a solubility of from 0.1 grams to 6 grams of material per gram of water;
   wherein the carrier substrate layer has a basis weight of 10 gsm and 50 gsm; each of the stimulation layers has a basis weight of 25 gsm to 500 gsm and each of the thermoplastic adhesive layers has a basis weight of 2 gsm to 25 gsm; and
   wherein the signal composite has a thickness in the z-direction of 0.25 mm and 5 mm, as measured by the Thickness Test.

19. The absorbent article of claim 18 wherein at least one of the stimulation layers further comprises a beneficial additive selected from surfactants, ion exchange resin particles, moisturizers, emollients, perfumes, fluid modifiers, odor control additives, pH buffering for the skin, vaginal health-care additives, coating materials for skin health, vitamins and medicines.

20. The absorbent article of claim 18 wherein at least one of the stimulation layers comprises stimulation material in the form of a cooling agent.

21. The absorbent article of claim 18 wherein each of the stimulation layers and each of the thermoplastic adhesive layers are respectfully coextensive in the longitudinal direction and in the transverse direction with each other.

* * * * *